(12) United States Patent
Dull et al.

(10) Patent No.: US 7,101,896 B2
(45) Date of Patent: *Sep. 5, 2006

(54) PHARMACEUTICAL COMPOSITIONS AND METHODS FOR USE

(75) Inventors: Gary Maurice Dull, Lewisville, NC (US); Jeffrey Daniel Schmitt, Winston-Salem, NC (US); Balwinder Singh Bhatti, Winston-Salem, NC (US); Craig Harrison Miller, Winston-Salem, NC (US)

(73) Assignee: Targacept, Inc., Winston-Salem, NC (US)

( * ) Notice: Subject to any disclaimer, the term of this patent is extended or adjusted under 35 U.S.C. 154(b) by 17 days.

This patent is subject to a terminal disclaimer.

(21) Appl. No.: 11/039,641

(22) Filed: Jan. 20, 2005

(65) Prior Publication Data

US 2005/0267111 A1 Dec. 1, 2005

Related U.S. Application Data

(63) Continuation of application No. 09/845,526, filed on Apr. 30, 2001, now Pat. No. 6,890,935, which is a continuation-in-part of application No. 09/431,700, filed on Nov. 1, 1999, now abandoned.

(51) Int. Cl.
C07D 401/06 (2006.01)
C07D 413/06 (2006.01)
A61K 31/4025 (2006.01)
A61K 31/4427 (2006.01)
A61K 31/4433 (2006.01)
A61K 31/4439 (2006.01)
A61P 25/28 (2006.01)

(52) U.S. Cl. .................. 514/318; 514/343; 514/231.5; 546/133; 546/187; 546/276.4; 546/279.4; 544/111

(58) Field of Classification Search ............... 546/133, 546/187, 276.4, 279.4; 544/111; 514/305, 514/318, 343
See application file for complete search history.

(56) References Cited

U.S. PATENT DOCUMENTS

| | | |
|---|---|---|
| 5,212,188 A | 5/1993 | Caldwell et al. |
| 5,217,975 A | 6/1993 | Wadsworth et al. |
| 5,219,849 A | 6/1993 | Lotti et al. |
| 5,276,043 A | 1/1994 | Lippiello et al. |
| 5,346,906 A | 9/1994 | Baker et al. |
| 5,510,355 A | 4/1996 | Bencherif et al. |
| 5,583,140 A | 12/1996 | Bencherif et al. |
| 5,597,919 A | 1/1997 | Dull et al. |
| 5,604,231 A | 2/1997 | Smith et al. |
| 5,616,707 A | 4/1997 | Crooks et al. |
| 5,616,716 A | 4/1997 | Dull et al. |
| 5,663,356 A | 9/1997 | Ruecroft et al. |
| 5,731,323 A | 3/1998 | Whittamore |
| 5,780,437 A | 7/1998 | Goulet et al. |
| 5,811,442 A | 9/1998 | Bencherif et al. |
| 5,824,692 A | 10/1998 | Lippiello et al. |
| 5,849,764 A | 12/1998 | Goulet et al. |
| 5,852,041 A | 12/1998 | Cosford et al. |
| 5,859,004 A | 1/1999 | Olesen |
| 5,861,423 A | 1/1999 | Caldwell et al. |
| 5,952,339 A | 9/1999 | Bencherif et al. |
| 6,890,935 B1 * | 5/2005 | Dull et al. .................. 514/305 |

FOREIGN PATENT DOCUMENTS

| | | |
|---|---|---|
| WO | WO 94/08992 | 4/1994 |
| WO | WO 94/14805 | 7/1994 |
| WO | WO 95/03306 | 2/1995 |
| WO | WO 96/12711 | 5/1996 |
| WO | WO 97/01556 | 1/1997 |
| WO | WO 97/11072 | 3/1997 |
| WO | WO 98/25619 | 6/1998 |
| WO | WO 98/54181 | 12/1998 |
| WO | WO 99/00385 | 1/1999 |
| WO | WO 00/34276 | 6/2000 |
| WO | WO 99/32117 | 7/2000 |
| WO | WO 01/32264 | 5/2001 |

OTHER PUBLICATIONS

Barnes, Peter J., "Molecules in Focus Nuclear Factor-$^K$B," *Int. J. Biochem. Cell Biol.*, 29(6): 867-870 (1997).
Birtwistle, Jon, "The Role of Cigarettes and Nicotine in the Onset and Treatment of Ulcerative Colitis," *Postgrad Med J.*, 72: 714-718 (1996).
Ebadi, et al., "Neurotophins and Their Receptors in Nerve Injury and Repair," *Neurochem Int.*, 30(4/5): 347-374 (1997).
Hanisch et al., "Modulation of Hippocampal Acetylcholine Release: A Potent Central Action of Interleukin-2," *The Journal of Neuroscience*, 13(8): 3368-3374 (1993).
Holladay, et al., "Neuronal Nicotinic Acetylcholine Receptors as Targets for Drug Discovery," *J. Med. Chem.*, 40(26): 4169-4194 (1997).
Jonakait, G. Miller, "Neural-Immune Interactions in Sympathetic Ganglia," *TINS*, 16(10):419-423 (1993).

(Continued)

*Primary Examiner*—Venkataraman Balasubramanian
(74) *Attorney, Agent, or Firm*—Womble Carlyle Sandridge & Rice, PLLC

(57) ABSTRACT

The present invention relates to aryl olefinic azacyclic compounds and aryl acetylenic azacyclic compounds, including pyridyl olefinic cycloalkylamines and pyridyl acetylenic cycloalkylamines. The present invention also relates to prodrug derivatives of the compounds of the present invention.

8 Claims, No Drawings

OTHER PUBLICATIONS

Madretsma, et al., "In-Vivo Effect of Nicotine on Cytokine Production by Human Non-Adherent Monomuclear Cells," *European J. of Gastroen & Hepat*, 8(10): 1017-1020 (1996).

Madretsma, et al., "Nicotine Inhibits the in Vitro Production of Interleukin 2 and Tumour Necrosis Factor- α by Human Mononuclear Cells," *Immunopharmacology*, 35: 47-51 (1996).

Matthys, P. & Billiau, A., "Cytokines and Cachexia," *Nutrition*, 13: 763-770 (1997).

Olesen, et al., "Identification of Novel (Isoxazole)Methylene-1-Azabicyclic Compounds with High Affinity for the Central Nicotinic Cholinergic Receptor," *Bioorganic & Medicinal Chemistry Letters*, 7(15): 1963-1968 (1997).

Olivo, et al., "Syntheses of New Open-Ring and *homo*-Epibatidine Analogues from Tropinone," *J. Org. Chem.*, 64(13): 4966-4968 (1999).

Peacock, et al., "The Effect of Nicotine on Reproduction and Attachment of Human Gingival Fibroblasts in Vitro," *J. Periodontal*, 64(7): 658-665 (1993).

Pullan, Rupert D., "Colonic Mucus, Smoking and Ulcerative Colitis," *Ann R. Coll. Sur Engl.*, 78: 85-91 (1996).

Pullan, et al., "Transdermal Nicotine for Active Ulcerative Colitis," *The New England Journal of Medicine*, 330(12):811-815 (1994).

Sandborn et al., "Nicotine Tartrate Liquid enemas for Mildly to Moderately Active Left-Side Ulcerative Colitis Unresponsive to First-Line Therapy: A Pilot Study," *Ailment Pharmacol. Ther.*, 11 663-671 (1997).

Sartor, R. Balfour, M.D., "Pathogenesis and Immune Mechanisms of Chronic Inflammatory Bowel Diseases," *The American Journal of Gastroenterology*, 92: 12 5S-11S (1997).

Secor, H. & Seeman, J., "The Preparation of 'Elongated' Nicotine Analogues," *Heterocycles*, 24:6 1687-1698 (1986).

Silverstein et al., "Cigarette Smoking and Ulcerative Colitis: A Case-Control Study," *Mayo Clin. Proc.*, 69 425-429 (1994).

Van Dijk et al., "Nicotine Inhibits Cytokine Synthesis by Mouse Colonic Mucosa," *European Journal of Pharmacology*, 278 R11-R12 (1995).

Wallace, J. & Chin, B., "Inflammatory Mediators in Gastrointestinal Defense and Injury," *Proc. Soc. Exp. Biol. Med.*, 214 192-203 (1997).

Yanina et al., Khim.-Karm, 21:7 808-811 (1987).

Zijlstra et al., "Effect of Nicotine on Rectal Mucus and Mucosal Eicosanoids," *Gut*, 35 247-251 (1994).

Clementi, et al., "Neuronal nicotinic receptors, important new players in brain function," *European Journal of Pharmacology*, 393: 3-10, (2000).

Cheng, et al., "Synthesis and Binding of 6,7,9,9-tetrahydro-5H-pyridio[3,4-d]azepine and related ring-opened analogs at central nicotinic receptors," *J. Med. Chem., 34*: 177-190 (1999).

International Search Report for PCT/US02/13635, mailed May 20, 2003.

* cited by examiner

PHARMACEUTICAL COMPOSITIONS AND METHODS FOR USE

RELATED APPLICATIONS

This application is a continuation of U.S. application Ser. No. 09/845,526, filed Apr. 30, 2001, which is now U.S. Pat. No. 6,890,935, which issued on May 10, 2005, the disclosure of which is incorporated by reference herein in its entirety, which is a continuation-in-part of U.S. application Ser. No. 09/431,700, filed Nov. 1, 1999, now abandoned.

BACKGROUND OF THE INVENTION

The present invention relates to pharmaceutical compositions, particularly pharmaceutical compositions incorporating compounds that are capable of affecting nicotinic cholinergic receptors. More particularly, the present invention relates to compounds capable of activating nicotinic cholinergic receptors, for example, as agonists of specific nicotinic receptor subtypes. The present invention also relates to methods for treating a wide variety of conditions and disorders, particularly conditions and disorders associated with dysfunction of the central and autonomic nervous systems.

Nicotine has been proposed to have a number of pharmacological effects. See, for example, Pullan et al., *N. Engl. J. Med.* 330:811 (1994). Certain of those effects may be related to effects upon neurotransmitter release. See, for example, Sjak-shie et al., *Brain Res.* 624:295 (1993), where neuroprotective effects of nicotine are proposed. Release of acetylcholine and dopamine by neurons upon administration of nicotine has been reported by Rowell et al., *J. Neurochem.* 43:1593 (1984); Rapier et al., *J. Neurochem.* 50:1123 (1988); Sandor et al., *Brain Res.* 567:313 (1991) and Vizi, *Br. J. Pharmacol.* 47:765 (1973). Release of norepinephrine by neurons upon administration of nicotine has been reported by Hall et al., *Biochem. Pharmacol.* 21:1829 (1972). Release of serotonin by neurons upon administration of nicotine has been reported by Hery et al., *Arch. Int. Pharmacodyn. Ther.* 296:91 (1977). Release of glutamate by neurons upon administration of nicotine has been reported by Toth et al., *Neurochem Res.* 17:265 (1992). Confirmatory reports and additional recent studies have included the modulation in the Central Nervous System (CNS) of glutamate, nitric oxide, GABA, takykinins, cytokines and peptides (reviewed in Brioni et al., *Adv. Pharmacol.* 37:153 (1997)). In addition, nicotine reportedly potentiates the pharmacological behavior of certain pharmaceutical compositions used for the treatment of certain disorders. See, for example, Sanberg et al., *Pharmacol. Biochem. & Behavior* 46:303 (1993); Harsing et al., *J. Neurochem.* 59:48 (1993) and Hughes, *Proceedings from Intl. Symp. Nic.* S40 (1994). Furthermore, various other beneficial pharmacological effects of nicotine have been proposed. See, for example, Decina et al., *Biol. Psychiatry* 28:502 (1990); Wagner et al., *Pharmacopsychiatry* 21:301 (1988); Pomerleau et al., *Addictive Behaviors* 9:265 (1984); Onaivi et al., *Life Sci.* 54(3):193 (1994); Tripathi et al., *J. Pharmacol. Exp. Ther.* 221:91(1982) and Hamon, *Trends in Pharmacol. Res.* 15:36 (1994).

Various nicotinic compounds have been reported as being useful for treating a wide variety of conditions and disorders. See, for example, Williams et al., *Drug News Perspec.* 7(4):205 (1994); Arneric et al., *CNS Drug Rev.* 1(1):1 (1995); Arneric et al., *Exp. Opin. Invest. Drugs* 5(1):79 (1996); Bencherif et al., *J. Pharmacol. Exp. Ther.* 279:1413 (1996); Lippiello et al., *J. Pharmacol. Exp. Ther.* 279:1422 (1996); Damaj et al., *J. Pharmacol. Exp. Ther.* 291:390 (1999); Chiari et al., *Anesthesiology* 91:1447 (1999); Lavand'homme and Eisenbach, *Anesthesiology* 91:1455 (1999); Holladay et al., *J. Med. Chem* 40(28): 4169 (1997); Bannon et al., *Science* 279: 77 (1998); PCT WO 94/08992, PCT WO 96/31475, PCT WO 96/40682, and U.S. Pat. No. 5,583,140 to Bencherif et al., U.S. Pat. No. 5,597,919 to Dull et al., U.S. Pat. No. 5,604,231 to Smith et al. and U.S. Pat. No. 5,852,041 to Cosford et al. Nicotinic compounds are reported as being particularly useful for treating a wide variety of CNS disorders. Indeed, a wide variety of compounds have been reported to have therapeutic properties. See, for example, U.S. Pat. No. 5,1871,166 to Kikuchi et al., U.S. Pat. No. 5,672,601 to Cignarella, PCT WO 99/21834 and PCT WO 97/40049, UK Patent Application GB 2295387 and European Patent Application 297,858.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses, and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a deficiency of choline, dopamine, norepinephrine and/or serotonin. Relatively common CNS disorders include presenile dementia (early-onset Alzheimer's disease), senile dementia (dementia of the Alzheimer's type), micro-infarct dementia, AIDS-related dementia, Creutzfeld-Jakob disease, Pick's disease, Parkinsonism including Parkinson's disease, progressive supranuclear palsy, Huntington's chorea, tardive dyskinesia, hyperkinesia, mania, attention deficit disorder, anxiety, dyslexia, schizophrenia, depression, obsessive-compulsive disorders and Tourette's syndrome.

It would be desirable to provide a useful method for the prevention and treatment of a condition or disorder by administering a nicotinic compound to a patient susceptible to or suffering from such a condition or disorder. It would be highly beneficial to provide individuals suffering from certain disorders (e.g., CNS diseases) with interruption of the symptoms of those disorders by the administration of a pharmaceutical composition containing an active ingredient having nicotinic pharmacology and which has a beneficial effect (e.g., upon the functioning of the CNS), but which does not provide any significant associated side effects. It would be highly desirable to provide a pharmaceutical composition incorporating a compound which interacts with nicotinic receptors, such as those which have the potential to effect the functioning of the CNS, but, when employed in an amount sufficient to effect the functioning of the CNS, does not significantly effect those receptor subtypes which have the potential to induce undesirable side effects (e.g., appreciable activity at cardiovascular and skeletal muscle sites).

SUMMARY OF THE INVENTION

The present invention relates to aryl olefinic azacyclic compounds and aryl acetylenic azacyclic compounds, including pyridyl olefinic cycloalkylamines and pyridyl acetylenic cycloalkylamines. The present invention also relates to prodrug derivatives of the compounds of the present invention. The present invention also relates to methods of synthesizing compounds of the present invention. Exemplary compounds of the present invention include (S)-5-(pyrrolidin-2-ylethynyl)pyrimidine, (S)-3-(pyrrolidin-2-ylethynyl)pyridine, (S)-3-isopropoxy-5-(pyrrolidin-2-ylethynyl)pyridine, (S)-3-phenyl-5-(pyrrolidin-2-ylethynyl)pyridine, (S)-3-(4-methoxyphenoxy)-5-(pyrrolidin-2-ylethynyl)pyridine, (S)-3-cyclopentyloxy-5-(pyrrolidin-2-ylethynyl)pyridine, (S)-3-cyclohexyloxy-5-(pyrrolidin-2-ylethynyl)pyridine, (S)-3-(4-(pyrrolidine-1-sulfonyl) phenoxy)-5-(pyrrolidin-2-ylethynyl)pyridine, (S)-3-(3-pyridyloxy)-5-(pyrrolidin-2-ylethynyl)pyridine, (S)-3-(pyrrolidin-2-ylethynyl)-5-(tetrahydropyran-4-yloxy) pyridine, (S)-3-(3,5-dihydroxy)phenoxy-5-(pyrrolidin-2-ylethynyl)pyridine, (S)-N-(2-(5-pyrrolidin-2-ylethynylpyridin-3-yloxy)ethyl)benzamide, (S)-3-(pyrrolidin-2-ylethynyl)-5-(3-methylsulfonylphenoxy) pyridine, (E,S)-3-(4-hydroxyphenoxy)-5-(pyrrolidin-2-ylvinyl)pyridine, (E,S)-3-cyclopentyloxy-5-(pyrrolidin-2-ylvinyl)pyridine. The compounds of the present invention function as agonists and bind specifically to certain nicotinic receptors.

The present invention also relates to methods for the prevention or treatment of a wide variety of conditions or disorders, and particularly those disorders characterized by dysfunction of nicotinic cholinergic neurotransmission including disorders involving neuromodulation of neurotransmitter release, such as dopamine release. The present invention also relates to methods for the prevention or treatment of disorders, such as central nervous system (CNS) disorders, which are characterized by an alteration in normal neurotransmitter release. The present invention also relates to methods for the treatment of certain conditions (e.g., a method for alleviating pain). The methods involve administering to a subject an effective amount of a compound of the present invention. As such, the present invention relates to a method for using the compounds of the present invention for the manufacture of pharmaceutical compositions for the treatment of a wide variety of diseases and disorders.

The present invention, in another aspect, relates to a pharmaceutical composition comprising an effective amount of a compound of the present invention. Such a pharmaceutical composition incorporates a compound which, when employed in effective amounts, has the capability of interacting with relevant nicotinic receptor sites of a subject, and hence has the capability of acting as a therapeutic agent in the prevention or treatment of a wide variety of conditions and disorders, particularly those disorders characterized by an alteration in normal neurotransmitter release. Preferred pharmaceutical compositions comprise compounds of the present invention.

The pharmaceutical compositions of the present invention are useful for the prevention and treatment of disorders, such as CNS disorders, which are characterized by an alteration in normal neurotransmitter release. The pharmaceutical compositions provide therapeutic benefit to individuals suffering from such disorders and exhibiting clinical manifestations of such disorders in that the compounds within those compositions, when employed in effective amounts, have the potential to: (i) exhibit nicotinic pharmacology and affect relevant nicotinic receptors sites (e.g., act as a pharmacological agonist to activate nicotinic receptors), and/or (ii) modulate neurotransmitter secretion and thus prevent and suppress the symptoms associated with those diseases. In addition, the compounds are expected to have the potential to fulfill the following results for the patient: (i) to alter the number of nicotinic cholinergic receptors of the brain of the patient, (ii) to exhibit neuroprotective effects and (iii) to result in no appreciable adverse side effects when administered in effective amounts—side effects such as significant increases in blood pressure and heart rate, significant negative effects upon the gastrointestinal tract, and significant effects upon skeletal muscle. The pharmaceutical compositions of the present invention are believed to be safe and effective with regards to prevention and treatment of a wide variety of conditions and disorders.

The foregoing and other aspects of the present invention are explained in detail in the detailed description and examples set forth below.

DETAILED DESCRIPTION OF THE INVENTION

The compounds of the present invention include compounds of the formula:

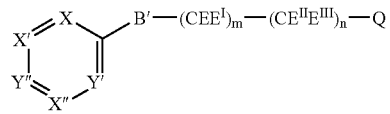

where Q is defined hereinafter; and each of X, X', X", Y' and Y" are individually nitrogen, nitrogen bonded to oxygen (e.g., an N-oxide or N—O functionality) or carbon bonded to a substituent species characterized as having a sigma m value greater than 0, often greater than 0.1, and generally greater than 0.2, and even greater than 0.3; less than 0 and generally less than −0.1; or 0; as determined in accordance with Hansch et al., *Chem. Rev.* 91:165 (1991). When any of X, X', X", Y' and Y" are carbon bonded to a substituent species, those substituent species typically have a sigma m value between about −0.3 and about 0.75, frequently between about −0.25 and about 0.6; and each sigma m value individually can be 0 or not equal to zero. Preferably, less than 4, more preferably less than 3, and most preferably 1 or 2 of X, X', X", Y' and Y" are nitrogen or nitrogen bonded to oxygen. In addition, it is highly preferred that not more than 1 of X, X', X", Y' and Y" be nitrogen bonded to oxygen; and it is preferred that if one of those species is nitrogen bonded to oxygen, that species is X". Typically, X' is CH, CR' or COR', where R' preferably is alkyl, cycloalkyl, heterocyclyl, aryl or heteroaryl, any of which may be further substituted as described hereinbelow. Most preferably, X" is nitrogen. In certain preferred circumstances, both X' and X" are nitrogen. Typically, X, Y' and Y" each are carbon bonded to a substituent species, and it is typical that X, Y' and Y" each are carbon bonded to a substituent species such as hydrogen. Typically, X is CH and Y' is CH.

The substituents of either X, X', X", Y' and Y" (when each respective X, X', X", Y' and Y" is carbon) can include alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, halo (e.g., F, Cl, Br, or I), —OR', —NR'R", —CF$_3$, —CN, —NO$_2$, —C$_2$R', —SR', —N$_3$, —C(=O)NR'R", —NR'C(=O)R", —C(=O)R', —C(=O) OR', —OC(=O)R', —O(CR'R")$_r$C(=O)R', —O(CR'R") $_r$NR'R"—O(CR'R")$_r$NR"C(=O)R', —O(CR'R") $_r$NR"SO$_2$R', —OC(=O)NR'R", —NR'C(=O)O R", —SO$_2$R', —SO$_2$NR'R", and —NR'SO$_2$R", where R' and R"

are individually hydrogen, lower alkyl, cycloalkyl, heterocyclyl, or an aromatic group-containing species and r is an integer from 1 to 6. R' and R" can together form a cycloalkyl functionality. Representative aromatic group-containing species include phenyl, benzyl, pyridinyl, pyrimidinyl, pyrazinyl, pyridazinyl, indolyl and quinolinyl. Other representative aromatic ring systems are set forth in Gibson et al., J. Med. Chem. 39:4065 (1996). When either R' or R" is a non-hydrogen substituent species, it may be further substituted, one or more times, by non-hydrogen substituent species, as described hereinbefore. Adjacent substituents of X, X', Y", X" and Y' (when adjacent X, X', Y", X" and Y' each are carbon bonded to a respective substituent component) can combine to form one or more saturated or unsaturated, substituted or unsubstituted carbocyclic or heterocyclic rings containing, but not limited to, ether, acetal, ketal, amine, ketone, lactone, lactam, carbamate, or urea functionalities.

B' is a substituted or unsubstituted two carbon bridging species; and typically can be acetylenic or ethylenic, preferably acetylenic. That is, B' can be selected from —CC— or —CR'=CR"—, wherein R' and R" are defined as hereinbefore, but R' and R" preferably each are hydrogen. When the two carbon bridging species is ethylenic, that species can have an (E) or (Z) form, but most preferably is (E). In addition, m is an integer and n is an integer such that the sum of m plus n is 0, 1, 2 or 3, preferably is 0, 1 or 2, and more preferably is 0 or 1.

E, E', E" and E'" individually represent hydrogen or a suitable non-hydrogen substituent (e.g., alkyl, substituted alkyl, halo-substituted alkyl, cycloalkyl, substituted cycloalkyl, heterocyclyl, substituted heterocyclyl, aryl, substituted aryl, alkylaryl, substituted alkylaryl, arylalkyl or substituted arylalkyl). E, E', E" and E'" are preferably lower alkyl (e.g., straight chain or branched alkyl including $C_1$–$C_8$, preferably $C_1$–$C_5$, such as methyl, ethyl, or isopropyl) or halo substituted lower alkyl (e.g., straight chain or branched alkyl including $C_1$–$C_8$, preferably $C_1$–$C_5$, such as trifluoromethyl or trichloromethyl). Generally all of E, E', E" and E'" are hydrogen, or at least one E, E', E" and E'" is non-hydrogen and the remaining E, E', E" and E'" are hydrogen. For example, when m is 1 and n is 0, E and E' each can be hydrogen, or E can be hydrogen and E' can be methyl; or when m is 1 and n is 1, E, E', E" and E'" all can be hydrogen, or E, E' and E" can be hydrogen and E'" can be methyl, or E', E" and E'" can be hydrogen and E can be methyl. Typically, the selection of m, n, E, E', E" and E'" is such that 0, 1 or 2, usually 0 or 1, and preferably 0, of the substituents designated as E, E', E" and E'" are non-hydrogen (e.g., substituents such as alkyl or halo-substituted alkyl). However, it is preferred that when m is 1 and n is 0, neither E nor E' are substituted or unsubstituted aryl, heteroaryl, benzhydryl or benzyl. Q is represented as follows:

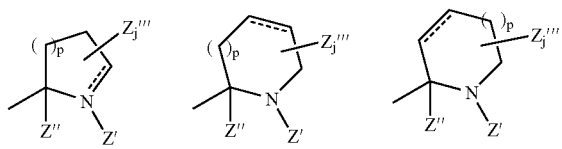

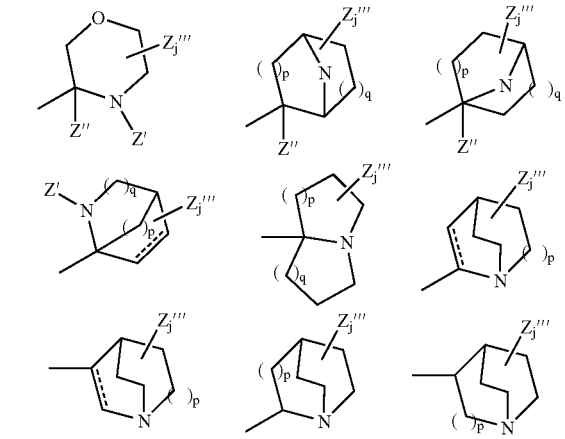

where $Z'''_j$ represents a suitable non-hydrogen substituent group (e.g., alkyl, substituted alkyl, halo-substituted alkyl, cycloalkyl, substituted cycloalkyl, heterocyclyl, substituted heterocyclyl, aryl, substituted aryl, alkylaryl, substituted alkylaryl, arylalkyl or substituted arylalkyl), but preferably alkyl. Z" represents hydrogen or lower alkyl, and Z' represents hydrogen, lower alkyl, acyl, alkoxycarbonyl or aryloxycarbonyl. Preferably, Z' is hydrogen or methyl and Z" is hydrogen. In addition, j is an integer from 0 to 5, preferably 0 or 1, most preferably 0; p is 0, 1 or 2, preferably 0 or 1, and most preferably 1; and q is 0, 1, 2 or 3, preferably 0 or 1, and most preferably 1. The dotted line indicates that the bond between the two atoms can be either a single or a double bond.

As employed herein, "alkyl" refers to straight chain or branched alkyl radicals including $C_1$–$C_8$, preferably $C_1$–$C_5$, such as methyl, ethyl, or isopropyl; "substituted alkyl" refers to alkyl radicals further bearing one or more substituent groups such as hydroxy, alkoxy, mercapto, aryl, heterocyclo, halo, amino, carboxyl, carbamyl, cyano, and the like; "alkenyl" refers to straight chain or branched hydrocarbon radicals including $C_1$–$C_8$, preferably $C_1$–$C_5$ and having at least one carbon-carbon double bond; "substituted alkenyl" refers to alkenyl radicals further bearing one or more substituent groups as defined above; "cycloalkyl" refers to saturated or unsaturated cyclic ring-containing radicals containing three to eight carbon atoms, preferably three to six carbon atoms; "substituted cycloalkyl" refers to cycloalkyl radicals further bearing one or more substituent groups as defined above; "aryl" refers to aromatic radicals having six to ten carbon atoms; "substituted aryl" refers to aryl radicals further bearing one or more substituent groups as defined above; "alkylaryl" refers to alkyl-substituted aryl radicals; "substituted alkylaryl" refers to alkylaryl radicals further bearing one or more substituent groups as defined above; "arylalkyl" refers to aryl-substituted alkyl radicals; "substituted arylalkyl" refers to arylalkyl radicals further bearing one or more substituent groups as defined above; "heterocyclyl" refers to saturated or unsaturated cyclic radicals containing one or more heteroatoms (e.g., O, N, S) as part of the ring structure and having two to seven carbon atoms in the ring; and "substituted heterocyclyl" refers to heterocyclyl radicals further bearing one or more substituent groups as defined above.

Compounds of the present invention can occur as stereoisomeric structures, and the present invention relates to racemic mixtures of such compounds as well as single enantiomer compounds.

Representative compounds useful in carrying out the present invention include the following:
(S)-5-(pyrrolidin-2-ylethynyl)pyrimidine
(R)-5-(pyrrolidin-2-ylethynyl)pyrimidine
(S)-3-(pyrrolidin-2-ylethynyl)pyridine
(R)-3-(pyrrolidin-2-ylethynyl)pyridine
(S)-3-isopropoxy-5-(pyrrolidin-2-ylethynyl)pyridine
(R)-3-isopropoxy-5-(pyrrolidin-2-ylethynyl)pyridine
(S)-3-phenyl-5-(pyrrolidin-2-ylethynyl)pyridine
(R)-3-phenyl-5-(pyrrolidin-2-ylethynyl)pyridine
(S)-3-(4-methoxyphenoxy)-5-(pyrrolidin-2-ylethynyl)pyridine
(R)-3-(4-methoxyphenoxy)-5-(pyrrolidin-2-ylethynyl)pyridine
(S)-3-cyclopentyloxy-5-(pyrrolidin-2-ylethynyl)pyridine
(R)-3-cyclopentyloxy-5-(pyrrolidin-2-ylethynyl)pyridine
(S)-3-cyclohexyloxy-5-(pyrrolidin-2-ylethynyl)pyridine
(RL)-3-cyclohexyloxy-5-(pyrrolidin-2-ylethynyl)pyridine
(S)-3-(4-(pyrrolidine-1-sulfonyl)phenoxy)-5-(pyrrolidin-2-ylethynyl)pyridine
(R)-3-(4-(pyrrolidine-1-sulfonyl)phenoxy)-5-(pyrrolidin-2-ylethynyl)pyridine
(S)-3-(3-pyridyloxy)-5-(pyrrolidin-2-ylethynyl)pyridine
(R)-3-(3-pyridyloxy)-5-(pyrrolidin-2-ylethynyl)pyridine
(S)-3-(pyrrolidin-2-ylethynyl)-5-(tetrahydropyran-4-yloxy)pyridine
(R)-3-(pyrrolidin-2-ylethynyl)-5-(tetrahydropyran-4-yloxy)pyridine
(S)-3-(3,5-dihydroxy)phenoxy-5-(pyrrolidin-2-ylethynyl)pyridine
(R)-3-(3,5-dihydroxy)phenoxy-5-(pyrrolidin-2-ylethynyl)pyridine
(S)-N-[2-(5-pyrrolidin-2-ylethynylpyridin-3-yloxy)ethyl]benzamide
(R)-N-[2-(5-pyrrolidin-2-ylethynylpyridin-3-yloxy)ethyl]benzamide
(S)-3-(pyrrolidin-2-ylethynyl)-5-(3-methylsulfonylphenoxy)pyridine
(R)-3-(pyrrolidin-2-ylethynyl)-5-(3-methylsulfonylphenoxy)pyridine
(E,S)-3-(4-hydroxyphenoxy)-5-(pyrrolidin-2-ylvinyl)pyridine
(E,R)-3-(4-hydroxyphenoxy)-5-(pyrrolidin-2-ylvinyl)pyridine
(E,S)-3-cyclopentyloxy-5-(pyrrolidin-2-ylvinyl)pyridine
(E,R)-3-cyclopentyloxy-5-(pyrrolidin-2-ylvinyl)pyridine
(S)-3-isopropoxy-5-(pyrrolidin-2-ylvinyl)pyridine
(R)-3-isopropoxy-5-(pyrrolidin-2-ylvinyl)pyridine
(S)-3-phenyl-5-(pyrrolidin-2-ylvinyl)pyridine
(R)-3-phenyl-5-(pyrrolidin-2-ylvinyl)pyridine
(S)-3-(4-methoxyphenoxy)-5-(pyrrolidin-2-ylvinyl)pyridine
(R)-3-(4-methoxyphenoxy)-5-(pyrrolidin-2-ylvinyl)pyridine
(S)-3-cyclopentyloxy-5-(pyrrolidin-2-ylvinyl)pyridine
(R)-3-cyclopentyloxy-5-(pyrrolidin-2-ylvinyl)pyridine
(S)-3-cyclohexyloxy-5-(pyrrolidin-2-ylvinyl)pyridine
(R)-3-cyclohexyloxy-5-(pyrrolidin-2-ylvinyl)pyridine
(S)-3-(4-(pyrrolidine-1-sulfonyl)phenoxy)-5-(pyrrolidin-2-ylvinyl)pyridine
(R)-3-(4-(pyrrolidine-1-sulfonyl)phenoxy)-5-(pyrrolidin-2-ylvinyl)pyridine
(S)-3-(3-pyridyloxy)-5-(pyrrolidin-2-ylvinyl)pyridine
(R)-3-(3-pyridyloxy)-5-(pyrrolidin-2-ylvinyl)pyridine
(S)-3-(pyrrolidin-2-ylvinyl)-5-(tetrahydropyran-4-yloxy)pyridine
(R)-3-(pyrrolidin-2-ylvinyl)-5-(tetrahydropyran-4-yloxy)pyridine
(S)-3-(3,5-dihydroxy)phenoxy-5-(pyrrolidin-2-ylvinyl)pyridine
(R)-3-(3,5-dihydroxy)phenoxy-5-(pyrrolidin-2-ylvinyl)pyridine
(S)-N-[2-(5-pyrrolidin-2-ylvinylpyridin-3-yloxy)ethyl]benzamide
(R)-N-[2-(5-pyrrolidin-2-ylvinylpyridin-3-yloxy)ethyl]benzamide
(S)-3-(pyrrolidin-2-ylvinyl)-5-(3-methylsulfonylphenoxy)pyridine
(R)-3-(pyrrolidin-2-ylvinyl)-5-(3-methylsulfonylphenoxy)pyridine
5-(2-(5-azabicyclo[3.3.0]octyl)ethynyl)pyridine
5-(2-(5-azabicyclo[3.3.0]octyl)ethynyl)-3-cyclopentyloxypyridine
5-(2-(5-azabicyclo[3.3.0]octyl)ethynyl)pyrimidine
(E)-5-(2-(3-pyridyl)vinyl)-1-azabicyclo[3.3.0]octane
(Z)-5-(2-(3-pyridyl)vinyl)-1-azabicyclo[3.3.0]octane
(E)-5-(2-(5-azabicyclo[3.3.0]octyl)vinyl)-3-cyclopentyloxypyridine
(Z)-5-(2-(5-azabicyclo[3.3.0]octyl)vinyl)-3-cyclopentyloxypyridine
(E)-5-(2-(5-azabicyclo[3.3.0]octyl)vinyl)pyrimidine
(Z)-5-(2-(5-azabicyclo[3.3.0]octyl)vinyl)pyrimidine
5-(2-(5-azabicyclo[3.3.0]octyl)ethyl)pyridine
5-(2-(5-azabicyclo[3.3.0]octyl)ethyl)-3-cyclopentyloxypyridine
5-(2-(5-azabicyclo[3.3.0]octyl)ethyl)pyrimidine The manner in which certain compounds of the present invention are synthesized can vary. Depending upon the enantiomeric purity of starting materials, compounds of the present invention can be prepared in either racemic form or in enantiomerically pure form. In one method, certain pyridyl olefinic pyrrolidine compounds can be prepared by using a palladium-catalyzed coupling reaction of a 3-bromopyridine or 3-iodopyridine with an olefin possessing a protected pyrrolidine functionality, such as (2S)-2-allyl-N-(tert-butoxycarbonyl)pyrrolidine, also known as (2S)-N-(tert-butoxycarbonyl)-2-(3-prop-1-enyl)pyrrolidine. Reaction conditions employing palladium(II) acetate, tri-o-tolylphosphine and triethylamine (so-called Heck conditions), similar to those described by Frank et al., *J. Org. Chem.* 43 (15): 2947 (1978) and Malek et al., *J. Org. Chem.* 47: 5395 (1982), can be used. The tert-butoxycarbonyl protecting group of the resulting reaction product, (2S)-(2E)-N-(tert-butoxycarbonyl)-2-(3-prop-1-(3-pyridyl)-1-enyl)pyrrolidine, can then be removed by treatment with a strong acid, such as trifluoroacetic acid, to produce (2S)-(2E)-2-(3-prop-1-(3-pyridyl)-1-enyl)pyrrolidine. The pyrrolidine ring can then be N-methylated using aqueous formaldehyde and sodium cyanoborohydride using methodology similar to that described by Abreo et al., *J. Med. Chem.* 39: 817 (1996) to afford (2S)-(2E)-2-(3-(1-methylpyrrolidin-2-yl)prop-1-enyl)pyridine. The aforementioned side chain, (2S)-2-allyl-N-(tert-butoxycarbonyl)pyrrolidine, can be prepared from commercially available (Aldrich Chemical Company) (2S)-2-pyrrolidinemethanol. The pyrrolidine nitrogen of the latter compound can be protected by treatment with di-tert-butyl dicarbonate in dichloromethane using triethylamine as a base to produce (2S)-N-(tert-butoxycarbonyl)-2-(hydroxymethyl)pyrrolidine. The latter compound can be treated with iodine, triphenylphosphine, and diethyl azodicarboxylate to give (2S)-N-(tert-butoxycarbonyl)-2-(iodomethyl)pyrrolidine. Treatment of the latter compound with vinylmagnesium bromide and copper(I) iodide produces the desired olefinic pyrrolidine, (2S)-2-allyl-N-(tert-butoxycarbonyl)pyrrolidine.

Since (2R)-2-pyrrolidinemethanol is also commercially available (Aldrich Chemical Company), the corresponding enantiomeric synthetic intermediates and compounds of the present invention, namely (2R)-2-allyl-N-(tert-butoxycarbonyl)pyrrolidine, (2R)-(2E)-N-(tert-butoxycarbonyl)-2-(3-prop-1-(3-pyridyl)-1-enyl)pyrrolidine, (2R)-(2E)-2-(3-prop-1-(3-pyridyl)-1-enyl)pyrrolidine and (2R)-(2E)-3-(3-(1-methylpyrrolidine-2-yl)prop-1-enyl)pyridine, can be prepared in a similar fashion. Alternatively, enantiomerically pure 2-pyrrolidinemethanol can be synthetically elaborated to the desired chiral olefinic pyrrolidine, 2-allyl-N-(tert-butoxycarbonyl)pyrrolidine using the methodology of Ikeda et al., *Heterocycles* 50: 31 (1999).

The corresponding propargyl linked compounds can also be synthesized from N-(tert-butoxycarbonyl)-2-(iodomethyl)pyrrolidine. Thus, treatment with lithium trimethylsilylacetylide, followed by deprotection using tetrabutylammonium fluoride, will afford N-(tert-butoxycarbonyl)-2-(propargyl)pyrrolidine. This material can be coupled to 3-bromopyridine using so-called Sonogashira conditions, typically employing tetrakis(triphenylphosphine)palladium (0) and copper(I) iodide as catalyst for the coupling. Procedures such as those reported by Evans and Bach, *Angew. Chem. Int. Ed.* 32:1326 (1993) and Yamanaka et al., *Chem. Pharm. Bull.* 29:3543 (1981) can be used. The product, N-(tert-butoxycarbonyl)-2-(3-prop-1-(3-pyridyl)-1-ynyl) pyrrolidine, can be deprotected by trifluoroacetic acid to give 2-(3-prop-1-(3-pyridyl)-1-ynyl)pyrrolidine.

The manner in which certain 5-substituted-pyridyl olefinic pyrrolidine compounds of the present invention are synthesized can vary. In one preferred method, a 5-substituted-3-halo-pyridine compound is subjected to a palladium-catalyzed reaction with an olefinic pyrrolidine compound such as (2S)-2-allyl-N-(tert-butoxycarbonyl)pyrrolidine as described above. Removal of the tert-butoxycarbonyl protecting group affords (2S)-(2E)-2-(3-prop)-1-(5-substituted-3-pyridyl)-1-enyl)pyrrolidine, which can subsequently be N-methylated using aqueous formaldehyde and formic acid. In this manner, a number of 5-substituted pyridyl compounds of the present invention can be prepared. In a similar fashion, if one employs a 5-halopyrimidine compound such as 5-bromopyrimidine in this Heck reaction sequence, then the corresponding enantiomerically pure pyrimidine compounds can be prepared, namely (2R)- and (2S)-(2E)-2-(3-prop-1-(5-pyrimidinyl)-1-enyl)pyrrolidine and (2R)- and (2S)-(2E)-5-(3-(1-methylpyrrolidin-2-yl)prop-1-enyl)pyrimidine.

In a similar manner, 2-allylquinuclidine can be subjected to a palladium-catalyzed coupling reaction with a 3-halopyridine, such as 3-bromopyridine or 3-iodopyridine, to afford 2-(1-(3-pyridyl)propen-3-yl)quinuclidine. The precursor, 2-allylquinuclidine can be prepared from 3-quinuclidinone (commercially available from Aldrich Chemical Company) by alkylation and modified Wolff-Kishner reduction. Thus, 3-quinuclidinone can be converted to the corresponding imine with isopropylamine and molecular sieves. See, for example, Forsyth et al., *J. Am. Chem. Soc.* 109:7270 (1987). Alkylation of the imine with lithium diisopropylamide and allyl bromide, followed by hydrolysis, produces 2-allyl-3-quinuclidinone. Removal of the carbonyl-protecting group can then be effected by converting the ketone into the p-toluenesulfonylhydrazone followed by reduction with sodium cyanoborohydride to afford 2-allylquinuclidine.

The manner in which certain pyridyl acetylenic pyrrolidine compounds of the present invention are synthesized can vary. In one method, a palladium-catalyzed reaction can be used for the coupling of a 3-bromopyridine or a 3-iodopyridine with an alkyne possessing a protected pyrrolidine functionality, such as (2S)-N-(tert-butoxycarbonyl)-2-propargylpyrrolidine. Reaction conditions employing tetrakis (triphenylphosphine)palladium(0), copper(I) iodide, a base such as triethylamine and an appropriate solvent, such as 1,2-dimethoxyethane or N,N-dimethylformamide, can be used. Alternatively, the methodology set forth in Bleicher et al., *Synlett.* 1115 (1995) can be used. The resulting coupling reaction product, (2S)-N-(tert-butoxycarbonyl)-2-(3-(3-pyridyl)prop-2-ynyl)pyrrolidine, can then be treated with a strong acid such as trifluoroacetic acid to remove the protecting group, producing (2S)-3-(3-pyrrolidin-2-ylprop-1-ynyl)pyridine. The latter compound can be N-methylated by heating with formaldehyde and formic acid to afford (2S)-3-(3-(1-methylpyrrolidin-2-yl)prop-1-ynyl)pyridine. The aforementioned alkyne, (2S)-N-(tert-butoxycarbonyl)-2-propargylpyrrolidine can be prepared by treatment of (2S)-N-(tert-butoxycarbonyl)-2-(iodomethyl)pyrrolidine (the synthesis of which has been previously described above) with the lithium salt of trimethylsilylacetylene or with lithium acetylide, ethylenediamine complex (commercially available from Aldrich Chemical Company) followed by desilylation, if necessary, using potassium fluoride in acetonitrile. The corresponding enantiomers, (2R)-3-(3-pyrrolidin-2-ylprop-1-ynyl)pyridine and (2R)-3-(3-(1-methylpyrrolidin-2-yl)prop-1-ynyl)pyridine can be synthesized from the enantiomeric alkyne, (2R)-N-(tert-butoxycarbonyl)-2-propargylpyrrolidine, which ultimately can be prepared from (2R)-2-pyrrolidinemethanol (available from Aldrich Chemical Company).

In addition, the shorter chain length analogs are readily prepared from (2S)-N-(tert-butoxycarbonyl)-2-(hydroxymethyl)pyrrolidine. A Swern oxidation using oxalyl chloride to produce the aldehyde (Swern et al., *J. Org. Chem.* 41:3329 (1976)) followed by conversion to the olefin, using the techniques described in Wittig et al., *Liebigs Ann.* 562:187 (1949), provides (2S)-N-(tert-butoxycarbonyl)-2-vinylpyrrolidine. The corresponding alkyne, (2S)-N-(tert-butoxycarbonyl)-2-(ethynyl)pyrrolidine, may be prepared by treatment of the aldehyde with carbon tetrabromide and triphenylphosphine followed by n-butyl lithium.

Compounds of the present invention possessing a shorter olefinic side chain can be prepared by a variety of methods. In one approach using similar palladium-catalyzed coupling methods, a 3-halopyridine, such as 3-bromopyridine or 3-iodopyridine, is coupled with (2S)-N-(tert-butoxycarbonyl)-2-vinylpyrrolidine. The latter olefinic pyrrolidine compound can be prepared according to the techniques described by Ikeda et al., supra, starting from commercially available (2S)-2-pyrrolidinemethanol. The protecting group can then be removed from the resulting reaction product, (2S)-(2E)-N-(tert-butoxycarbonyl)-3-(2-pyrrolidin-2ylvinyl)pyridine, using trifluoroacetic acid to give (2S)-(2E)-3-(2-pyrrolidin-2-ylvinyl)pyridine. The latter compound can be N-methylated using the previously described methodology. By using (2R)-2-pyrrolidinemethanol, the corresponding enantiomers of the above compounds can be prepared.

Certain compounds of the present invention possessing a shorter acetylenic side chain can be prepared by a variety of methods. In one synthetic approach, a 3-halopyridine such as 3-bromopyridine can be coupled with an alkyne possessing a protected pyrrolidine functionality such as (2S)-N-(tert-butoxycarbonyl)-2-ethynylpyrrolidine. Reaction conditions employing a palladium catalyst such as tetrakis (triphenylphosphine)palladium(0), copper(I) iodide, triethylamine and a solvent such as N,N-dimethylformamide can be used. The resulting reaction product, (2S)-N-(tert-butoxycarbonyl)-3-(2-pyrrolidin-2-ylethynyl)pyridine, can be treated with a strong acid such as trifluoroacetic acid to afford (2S)-3-(2-pyrrolidin-2-ylethynyl)pyridine. Treatment of the latter compound with formic acid and formaldehyde or formaldehyde and sodium cyanoborohydride affords the N-methyl analog, (2S)-3-(2-(1-methylpyrrolidin-2-yl)ethynyl)pyridine. The aforementioned alkyne, (2S)-N-(tert-butoxycarbonyl)-2-ethynylpyrrolidine, can be prepared from N-(tert-butoxycarbonyl)-(S)-proline according to the methods described in WO 97/05139 to Elliot et al. By using the enantiomeric alkyne, (2R)-N-(tert-butoxycarbonyl)-2-ethynylpyrrolidine, prepared from N-(tert-butoxycarbonyl)-(R)-proline, the enantiomers of the above compounds of the present invention can be prepared.

There are a number of methods by which the (Z)-olefinic isomers of pyridyl olefinic pyrrolidine compounds can be synthetically produced. In one approach, these (Z)-olefinic isomers can be prepared by the controlled hydrogenation of the corresponding alkynyl compounds (e.g., a 3-(3-pyrrolidin-2-ylprop-1-ynyl)pyridine-type compound) using commercially available Lindlar catalyst (Aldrich Chemical Company) using the methodology set forth in Lindlar et al., *Org. Syn.* 46: 89 (1966).

A great variety of 5-substituted-3-bromopyridines can be used in either Sonogashira (with alkynes) or Heck (with alkenes) coupling reactions, as described previously. These 5-substituted-3-bromopyridines can be readily made from commercially available 3,5-dibromopyridine. Thus, Suzuki coupling of 3,5-dibromopyridine with arylboronic acids, in the presence of a palladium catalyst, gives 5-aryl-3-bromopyridines. Procedures such as those described by Guillier, et al., *J. Org. Chem.* 60: 292 (1995) can be used. This methodology has been used synthesize 5-phenyl and 5-(4-phenoxyphenyl) analogs. In another example, 3-bromo-5-isopropoxypyridine is readily prepared from 3,5-dibromopyridine and sodium isopropoxide. This methodology is extremely general and has been utilized to prepare a variety of 5-alkoxy- and 5-aryloxy-substituted analogs including 5-phenoxy-, 5-cyclopentyloxy-, 5-cyclohexyloxy-, 5-(4-methoxyphenoxy)-, 5-(3,5-dimethoxyphenoxy)- and 3-pyridyloxy-substituted analogs. In each case, the 5-alkoxy- or 5-aryloxy-3-bromopyridine is made by reaction of 3,5-dibromopyridine with the corresponding sodium alkoxide or sodium aryloxide. The simple 5-alkoxy-3-bromopyridines (methoxy, ethoxy, isopropoxy) can be readily hydrolyzed, by the action of hydrobromic acid, to 5-hydroxy-3-bromopyridine. This intermediate can also be coupled to both alkenes and alkynes in palladium-catalyzed processes, providing 5-hydroxy analogs. Alkylthiolates and arylthiolates will also react with 3,5-dibromopyridine to give 5-alkylthio- and 5-arlythio-3-bromopyridines. These sulfur containing species can be used in palladium-catalyzed coupling reactions as well.

The 5-hydroxy-3-bromopyridine intermediate is also versatile, being a substrate for several different alkylation/arylation reactions. Thus, it can be employed in nucleophilic aromatic substitution reactions with electron-deficient aromatic rings. For instance, reaction with 1-((4-fluorophenyl)sulfonyl)pyrrolidine, in the presence of carbonate base, gives 3-bromo-5-(4-(pyrrolidine-1-sulfonyl)phenoxy)pyridine. Other aromatic halides can be employed as electrophiles (e.g., 4-fluorobenzonitrile and 4-chloropyrimidine).

The Mitsunobu reaction of 5-hydroxy-3-bromopyridine with various alcohols provides a route to complex alkoxy substituents. Thus, 3-bromo-5-(tetrahydropyran-4-yloxy) pyridine can be made by reaction of 5-hydroxy-3-bromopyridine with tetrahydropyran-4-ol, using triphenylphosphine and diethyl azodicarboxylate, as described in Mitsunobu et al., *Bull. Chem. Soc. Jpn.* 40:2380 (1967) and Mitsunobu, *Synthesis* 1 (1981). Other complex alcohol substrates can be employed in this reaction (e.g., N-phenyl-4-piperidinol and (2S)-N-trifluoroacetyl-2-pyrrolidinemethanol).

Williamson ether synthesis can also be used to generate complex alkoxy analogs. Thus, reaction of 5-hydroxy-3-bromopyridine with N-(2-chloroethyl)phthalimide gives 3-bromo-5-(2-phthalimidoethoxy)pyridine. Subsequently, the phthaloyl protecting group can be removed and a variety of amides produced from the resulting amine.

The manner in which compounds of the present invention can be synthesized can vary. In another approach, 5-bromonicotinic acid is a suitable precursor of various 5-substituted-3-bromopyridines. The carboxylic acid functionality can be converted into a variety of derivative functionalities, using methods familiar to those skilled in the art of organic synthesis. Thus, the corresponding esters and amides (both unsubstituted and substituted) are readily prepared from the acid. These can be used directly in palladium-catalyzed coupling reactions or further transformed to other derivatives. For instance, certain amides are known to readily undergo nucleophilic acyl substitution to produce ketones. Thus, the so-called Weinreb amides (N-methoxy-N-methylamides) react with aryllithium reagents to produce the corresponding diaryl ketones. For example, see Selnick, et al., *Tetrahedron Lett.* 34: 2043 (1993). In this manner 5-(arylcarbonyl)-3-bromopyridines can be made. Such compounds can also be synthesized by conversion of 5-bromonicotinic acid to the acyl chloride (using thionyl chloride), followed by Friedel-Crafts-type acylation. See, for example, Villani and King, *Org. Syn. Coll. Vol.* 4: 88 (1963). The 5-(arylcarbonyl)-3-bromo-pyridines, in turn, serve as substrates for the palladium-catalyzed coupling reactions, leading to compounds of the present invention.

5-Bromonicotinamide, produced from acid chloride by reaction with ammonia, can be converted by the action of sodium hypochloride into 3-amino-5-bromopyridine. This material can be coupled, in a palladium-catalyzed process, to the N-(tert-butoxycarbonyl)azacyclic alkenes and alkynes previously described to give compounds of the present invention. The resulting 5-amino substituted compounds can be further transformed, by diazonium ion chemistry, to give various 5-substituted analogs. Among the other 5-substituted analogs that can be produced from 5-diazonium salt intermediates are: 5-hydroxy analogs, 5-alkoxy analogs, 5-fluoro analogs, 5-chloro analogs, 5-bromo analogs, 5-iodo analogs, 5-cyano analogs and 5-mercapto analogs. These compounds can be synthesized using the general techniques set forth in Zwart et al., *Recueil Trav. Chim. Pays-Bas* 74:1062 (1955). For example, 5-hydroxy substituted analogs can be prepared from the reaction of the corresponding 5-diazonium salt intermediates with water. 5-Alkoxy analogs can be made from the reaction of the diazonium salts with alcohols. 5-Fluoro substituted analogs can be prepared from the reaction of the 5-diazonium salt intermediates with fluoroboric acid. 5-Chloro substituted analogs can be prepared from the reaction of the 5-amino compounds with sodium nitrite and hydrochloric acid in the presence of copper chloride. 5-Cyano substituted analogs can be prepared from the reaction of the corresponding 5-diazonium salt intermediates with potassium copper cyanide. Appropriate 5-diazonium salt intermediates can also be used for the synthesis of mercapto-substituted analogs using the general techniques described in Hoffman et al., *J. Med. Chem.* 36: 953 (1993). The 5-mercapto-substituted analogs can in turn be converted to the 5-alkylthio-substituted analogs by reaction with sodium hydride and an appropriate alkyl bromide. 5-Acylamido analogs of the aforementioned compounds can be prepared by reaction of the corresponding 5-amino compounds with an appropriate acid anhydride or acid chloride using techniques known to those skilled in the art of organic synthesis.

5-Hydroxy-substituted analogs of the aforementioned compounds can be used to prepare corresponding 5-alkanoyloxy-substituted compounds by reaction with the appropriate acid, acid chloride, or acid anhydride. 5-Cyano-substituted analogs of the aforementioned compounds can be hydrolyzed to afford the corresponding 5-carboxamido-substituted compounds. Further hydrolysis results in formation of the corresponding 5-carboxylic acid-substituted analogs. Reduction of the 5-cyano-substituted analogs with lithium aluminum hydride yields the corresponding 5-aminomethyl analogs. 5-Acyl-substituted analogs can be prepared from corresponding 5-carboxylic acid-substituted analogs by reaction with an appropriate alkyl lithium using techniques known to those skilled in the art.

5-Carboxylic acid-substituted analogs of the aforementioned compounds can be converted to the corresponding esters by reaction with an appropriate alcohol and acid catalyst. Compounds with an ester group at the 5-pyridyl position can be reduced with sodium borohydride or lithium aluminum hydride to produce the corresponding 5-hydroxymethyl-substituted analogs. These analogs in turn can be converted to compounds bearing an ether moiety at the 5-pyridyl position by reaction with sodium hydride and an appropriate alkyl halide, using conventional techniques. Alternatively, the 5-hydroxymethyl-substituted analogs can be reacted with tosyl chloride to provide the corresponding 5-tosyloxymethyl analogs. The 5-carboxylic acid-substituted analogs can also be converted to the corresponding 5-alkylaminoacyl analogs by reaction with an appropriate alkylamine and thionyl chloride.

5-Tosyloxymethyl-substituted analogs of the aforementioned compounds can be converted to the corresponding 5-methyl-substituted compounds by reduction with lithium aluminum hydride. 5-Tosyloxymethyl-substituted analogs of the aforementioned compounds can also be used to produce 5-alkyl-substituted analogs via reaction with an alkyllithium. 5-Hydroxy-substituted analogs of the aforementioned compounds can be used to prepare 5-N-alkylcaroamoyloxy-substituted compounds by reaction with N-alkylisocyanates. 5-Amino-substituted analogs of the aforementioned compounds can be used to prepare 5-N-alkoxycarboxamido-substituted compounds by reaction with alkyl chloroformate esters, using techniques known to those skilled in the art of organic synthesis.

The manner in which certain compounds of the present invention are prepared can vary. For example, compounds that possess certain fused-ring heterocycles can be prepared by the Heck or Sonogashira reactions. Such compounds can be synthesized by the palladium-catalyzed coupling of a bromo-heterocyclic compound, such as 6-bromo-2-methyl-1H-imidazo[4,5-b]pyridine, with the previously mentioned N-(tert-butoxycarbonyl)-protected olefinic or acetylenic amines, such (2S)-2-vinyl-N-(tert-butoxycarbonyl)pyrrolidine or (2S)-2-ethynyl-N-(tert-butoxycarbonyl)pyrrolidine. Typically, the types of procedures set forth in Frank et al., *J. Org. Chem.* 43: 2947 (1978) and Malek et al., *J. Org. Chem.* 47: 5395 (1982) involving a palladium-catalyzed coupling of an olefin and an aromatic halide are used for the coupling reaction. Procedures such as those reported by Evans and Bach, *Angew. Chem. Int. Ed.* 32:1326 (1993) and Yamanaka et al., *Chem. Pharm. Bull.* 29:3543 (1981) for the coupling of alkynes to aromatic halides can be used. The resulting tert-butoxycarbonyl protected intermediate can be deprotected by treatment with a strong acid, such as trifluoroacetic acid. The aforementioned bromo-imidazopyridine, 6-bromo-2-methyl-1H-imidazo[4,5-b]pyridine can be prepared yield by heating 2,3-diamino-5-bromopyridine with acetic acid in polyphosphoric acid according to the methods described by Dubey et al., *Indian J. Chem.* 16B(6):531 (1978). 2,3-Diamino-5-bromopyridine can be prepared yield by heating 2-amino-5-bromo-3-nitropyridine (commercially available from Aldrich Chemical Company and Lancaster Synthesis, Inc) with tin(II) chloride dihydrate in boiling ethanol according to the techniques described by Cai et al., *J. Med. Chem.* 40(22): 3679 (1997).

In another example, a bromo fused-ring heterocycle, such as 6-bromo-1,3-dioxolo[4,5-b]pyridine, can be coupled with the previously mentioned N-(tert-butoxycarbonyl) protected olefinic or acetylenic azacyclic compounds using the Heck or Sonogashira reactions. The resulting intermediate can be deprotected with a strong acid such as trifluoroacetic acid. The aforementioned bromo compound, 6-bromo-1,3-dioxolo[4,5-b]pyridine, can be synthesized from 5-bromo-2,3-dihydroxypyridine, also known as 5-bromo-3-hydroxy-2(1H)-pyridinone, via a methylenation procedure using bromochloromethane in the presence of potassium carbonate and N,N-dimethylformamide according to the methodology of Dallacker et al., *Z. Naturforsch.* 34 b:1729 (1979). 5-Bromo-2,3-dihydroxypyridine can be prepared from furfural (2-furaldehyde, commercially available from Aldrich Chemical Company and Lancaster Synthesis, Inc) using the methods described in Dallacker et al., supra. Alternatively, 5-bromo-2,3-dihydroxypyridine can be prepared according to the techniques described in EP 0081745 to Rose and Maak.

In another example of a compound that possesses a fused-ring heterocycle, the bromo compound 7-bromo-2,3-dihydro-1,4-dioxino[2,3-b]pyridine (also known as 7-bromo-5-aza-4-oxachromane) can be condensed with the previously mentioned azacyclic alkenes and alkynes. The resulting compound can be deprotected with a strong acid such as trifluoroacetic acid. 7-Bromo-2,3-dihydro-1,4-dioxino[2,3-b]pyridine can be prepared by treating 5-bromo-2,3-dihydroxypyridine with 1,2-dibromoethane and potassium carbonate in N,N-dimethylformamide according to the methodology of Dallacker et al., supra. 5-Bromo-2,3-dihydroxypyridine can be prepared from furfural as described above.

Other polycyclic aromatic compounds of the present invention can be prepared by the Heck or Sonogashira reactions. Thus, certain compounds can be synthesized by the palladium-catalyzed coupling of a bromo fused-ring heterocycle, such as 6-bromo-1H-imidazo[4,5-b]pyridine-2-thiol, with the previously mentioned olefinic and acetylenic azacycles. The intermediate resulting from the coupling reaction can be subjected to treatment with a strong acid, such as trifluoroacetic acid, so remove the protecting group. The aforementioned bromo compound, 6-bromo-1H-imidazo[4,5-b]pyridine-2-thiol, can be prepared by treating 6-bromo-1H-imidazo[4,5-b]pyridine with sulfur at 230–260° C. according to the methods described in Yutilov, *Khim. Geterotsikl Doedin.* 6: 799 (1988). 6-Bromo-1H-imidazo[4,5-b]pyridine can be obtained from Sigma-Aldrich Chemical Company. Alternatively, 6-bromo-1H-imidazo[4,5-b]pyridine can be prepared by treating 2,3-diamino-5-bromopyridine with formic acid in polyphosphoric acid using methodology similar to that described by Dubey et al., supra. 2,3-Diamino-5-bromopyridine can be prepared by heating 2-amino-5-bromo-3-nitropyridine (commercially available from Aldrich Chemical Company and Lancaster Synthesis, Inc) with tin(II) chloride dihydrate in boiling ethanol according to the techniques described by Cai et al., supra. Alternatively, 6-bromo-1H-imidazo[4,5-b]pyridine-2-thiol can be prepared by heating 2,3-diamino-5-bromopyridine with $K^+$-SCSOEt in aqueous ethanol using methodology similar to that described by Kuhler et al., *J. Med. Chem.* 38(25): 4906 (1995). 2,3-Diamino-5-bromopyridine can be prepared from 2-amino-5-bromo-3-nitropyridine as described above.

In a related example, 6-bromo-2-phenylmethylthio-1H-imidazo[4,5-b]pyridine can be coupled via Heck or Sonogashira reactions with the previously mentioned olefinic and acetylenic azacycles. The resulting intermediate can be subjected to treatment with a strong acid, such as trifluoroacetic acid, to remove the protecting group. 6-Bromo-2-phenylmethylthio-1H-imidazo[4,5-b]pyridine can be prepared by alkylating the previously described 6-bromo-1H-imidazo[4,5-b]pyridine-2-thiol with benzyl bromide in the presence of potassium carbonate and N,N-dimethylformamide.

In another example, 6-bromooxazolo[4,5-b]pyridine can be subjected to palladium-catalyzed coupling and deprotection of the resulting intermediate with trifluoroacetic acid. 6-Bromooxazolo[4,5-b]pyridine can be produced from 2-amino-5-bromo-3-pyridinol by condensation with formic acid or a trialkyl orthoformate, using methodology similar to that of Viaud et al., *Heterocycles* 41: 2799 (1995). The use of other carboxylic acids produces 2-substituted-6-bromooxazolo[4,5-b]pyridines, which are also substrates for the Heck and Sonogashira reactions. The synthesis of 2-amino-5-bromo-3-pyridinol proceeds from furfurylamine (Aldrich Chemical Company). Thus, 5-bromo-3-pyridinol (produced from furfurylamine according to U.S. Pat. No. 4,192,946) can be chlorinated, using methods described by Koch et al., *Synthesis*, 499 (1990), to give 2-chloro-5-bromo-3-pyridinol, which in turn can be converted to 2-amino-5-bromo-3-pyridinol by treatment with ammonia.

5-Bromooxazolo[5,4-b]pyridine, isomeric by orientation of ring fusion to the previously described 6-bromooxazolo[4,5-b]pyridine, can also be used in the Heck and Sonogashira coupling and subsequent deprotection. 5-Bromooxazolo[5,4-b]pyridine is synthesized from 3-amino-5-bromo-2-pyridinol (3-amino-5-bromo-2-pyridone) by the condensation with formic acid (or a derivative thereof) as described above. 3-Amino-5-bromo-2-pyridinol can be made by bromination (using techniques described by Batkowski, *Rocz. Chem.* 41: 729 (1967)) and subsequent tin(II) chloride reduction (according to the method described by Cai et al., supra) of commercially available 3-nitro-2-pyridinol (Aldrich Chemical Company).

Other polycyclic aromatic compounds of the present invention can be prepared by the Heck and Sonogashira reactions. Thus, both 5-bromofuro[2,3-b]pyridine and 5-bromo-1H-pyrrolo[2,3-b]pyridine can undergo palladium-catalyzed coupling with the previously described olefinic and acetylenic azacycles. Subsequent removal of the tert-butoxycarbonyl group can be achieved with trifluoroacetic acid. The aforementioned 5-bromofuro[2,3-b]pyridine and 5-bromo-1H-pyrrolo[2,3-b]pyridine can be made from 2,3-dihydrofuro[2,3-b]pyridine and 2,3-dihydropyrrolo[2,3-b]pyridine respectively, by bromination (bromine and sodium bicarbonate in methanol) and dehydrogenation (2,3-dichloro-5,6-dicyano-1,4-benzoquinone), using chemistry described by Taylor et al., *Tetrahedron* 43: 5145 (1987). 2,3-Dihydrofuro[2,3-b]pyridine and 2,3-dihydropyrrolo[2,3-b]pyridine are, in turn, made from 2-chloropyrimidine (Aldrich Chemical Company) by nucleophilic displacement of the chloride (with the sodium salt of 3-butyn-1-ol or with 4-amino-1-butyne) and subsequent intramolecular Diels-Alder reaction, as described by Frissen et al., *Tetrahedron* 45: 803 (1989). Using similar chemistry, 2,3-dihydrofuro[2,3-b]pyridine and 2,3-dihydropyrrolo[2,3-b]pyridine are also produced from 3-methylthio-1,2,4-triazene (Taylor et al., supra), which in turn is made from glyoxal and S-methylthiosemicarbazide as described by Paudler et al., *J Heterocyclic Chem.* 7: 767 (1970).

Brominated dihydrofuropyridines, dihydropyrrolopyridines, and dihydropyranopyridines are also substrates for the palladium-catalyzed coupling. For instance, both 5-bromo-2,3-dihydrofuro[2,3-b]pyridine and 5-bromo-2,3-dihydropyrrolo[2,3-b]pyridine (from bromination of 2,3-dihydrofuro[2,3-b]pyridine and 2,3-dihydropyrrolo[2,3-b]pyridine, as described above) can be coupled with the previously mentioned olefinic or acetylenic azacyamine side chain in a Heck process and subsequent deprotection. Similarly, 6-bromo-2,3-dihydrofuro[3,2-b]pyridine (isomeric at the ring fusion with the [2,3-b]system) can also be used in a Heck process. The aforementioned 6-bromo-2,3-dihydrofuro[3,2-b]pyridine can be made from 5-bromo-2-methyl-3-pyridinol by sequential treatment with two equivalents of lithium diisopropylamide (to generate the 2-methylenyl, 3-oxy dianion) and one equivalent of dibromomethane. Alternatively, using chemistry similar to that described by Koller et al., *Synth. Commun.* 25: 2963 (1995), the silyl-protected pyridinol (5-bromo-2-methyl-3-trimethylsilyloxypyridine) can be treated sequentially with one equivalent of lithium diisopropylamide and an alkyl or aryl aldehyde to produce a 2-(2-(1-alkyl- or 1-aryl-1-hydroxy)ethyl)-5-bromo-3-(trimethylsilyloxy)pyridine. Such materials can be converted, by methods (such as acid catalyzed cyclization or the Williamson synthesis) known to those skilled in the art, into the corresponding cyclic ethers 2-alkyl- or 2-aryl-6-bromo-2,3-dihydrofuro[3,2-b]pyridines. Similar chemistry, in which epoxides (instead of aldehydes) are used in reaction with the pyridylmethyl carbanion, leads to 2-alkyl- and 2-aryl-7-bromo-2,3-dihydropyrano[3,2-b]pyridines. These 2-substituted, brominated dihydrofuro- and dihydropyranopyridines are also substrates for the Heck reaction. For instance, 6-bromo-2,3-dihydro-2-phenylfuro[3,2-b]pyridine can be coupled in a palladium-catalyzed process and the coupling product treated with trifluoroacetic acid to deprotect.

The 5-bromo-2-methyl-3-pyridinol, required for the syntheses of the brominated dihydrofuro- and dihydropyranopyridines, is produced by standard transformations of commercially available materials. Thus, 2-methylnicotinic acid (Aldrich Chemical Company) can be converted by sequential treatment with thionyl chloride, bromine, and ammonia, as described by Greco et al., *J Het. Chem.* 7: 761 (1970), into 5-bromo-2-methylnicotinamide. Hofmann rearrangement of 5-bromo-2-methylnicotinamide with hypochlorite will give 3-amino-5-bromo-2-methylpyridine, which can be converted to 5-bromo-2-methyl-3-pyridinol by diazotization with sodium nitrite in aqueous sulfuric acid. Alternatively, alanine ethyl ester (Aldrich Chemical Company) is converted (using ethyl formate) into its N-formyl derivative, which is then converted to 5-ethoxy-4-methyloxazole using phosphorous pentoxide (see Takeo et al., Japan Patent No. 45,012,732). A Diels-Alder reaction of 5-ethoxy-4-methyloxazole with acrylonitrile gives 5-hydroxy-6-methylnicotinonitrile, as described by Yoshikawa et al., *Chem. Pharm. Bull.* 13: 873 (1965), which is converted to 5-amino-2-methyl-3-pyridinol by hydration (nitrile→amide) and Hoffman rearrangement (see Morisawa et al., *Agr. Biol. Chem.* 39: 1275 (1975)). The 5-amino-2-methyl-3-pyridinol can then be converted, by diazotization in the presence of copper (I) bromide, to the desired 5-bromo-2-methyl-3-pyridinol.

The manner in which certain aryl substituted olefinic amine compounds possessing an azetidinyl moiety are synthesized can vary. Using one synthetic approach, 3-(2-(2-azetidinyl)vinyl)pyridine can be synthesized starting from commercially azetidine-4-carboxylic acid (Aldrich Chemical Company). Azetidine-2-carboxylic acid can be reduced by any of a number of methods common to the art, such as treatment with lithium aluminum hydride to give azetidine-2-methanol. Protection of the azetidinyl nitrogen of the latter compound can be accomplished by treatment with tert-butylpyrocarbonate and base to give N-(tert-butoxycarbonyl)azetidine-2-methanol, using methodology similar to that described by Carpino et al., *Acc. Chem. Res.* 6:191 (1973). This alcohol can be converted to the alkyl iodide using diethyl azodicarboxylate, triphenylphosphine and iodine according to the procedure of Mitsunobu described previously. Treatment of N-(tert-butoxycarbonyl)-2-(iodomethyl) azetidine with magnesium under anhydrous conditions followed by pyridine-3-carboxaldehyde affords the Grignard product, N-(tert-butoxycarbonyl)-2-(2-azetidinyl)-1-(3-pyridyl)ethan-1-ol. Treatment of the latter compound with methanesulfonyl chloride gives the O-mesylate, which can in turn be eliminated to give N-(tert-butoxycarbonyl)-3-(2-(2-azetidinyl)vinyl)pyridine using 1,8-diazabicyclo[5.4.0] undec-7-ene, in accordance with the method described by Wolkoff, *J. Org. Chem.* 47:1944 (1982). Finally, the protecting group can be removed under acidic conditions, such as treatment with trifluoroacetic acid, to give the desired product 3-(2-(2-azetidinyl)vinyl)pyridine.

The manner in which certain aryl-substituted olefinic amine compounds possessing an azabicyclo[2.2.1]heptane functionality are synthesized can vary. 2-(2-(3-Pyridyl)vinyl-7-azabicyclo[2.2.1]heptane can be synthesized starting with ethyl 7-aza-7-(ethoxycarbonyl)bicyclo[2.2.1]heptane-2-carboxylate which can be generated from commercially available tropinone (Lancaster Chemical Company) according to the method of Badio et al., *Eur. J. Pharmacol.* 321:865 (1997). This compound can then be reduced to ethyl 7-aza-2-(hydroxymethyl)bicyclo[2.2.1]heptane-7-carboxylate using excess diisobutylaluminum hydride. The resulting alcohol can then be converted to ethyl 7-aza-2-(iodomethyl) bicyclo[2.2.1]heptane-7-carboxylate using diethyl azodicarboxylate, triphenylphosphine and iodine in a Mitsunobu reaction. Conversion of ethyl 7-aza-2-(iodomethyl)bicyclo [2.2.1]heptane-7-carboxylate to the magnesium Grignard reagent, followed by reaction with pyridine 3-carboxaldehyde affords the alcohol, ethyl 2-(2-(3-pyridyl)-2-hydroxyethyl)-7-azabicyclo[2.2.1]heptane-7-carboxylate. Treatment of the latter compound with methanesulfonyl chloride yields the O-mesylate, which can in turn be eliminated to give ethyl 2-(2-(3-pyridyl)vinyl-7-azabicyclo[2.2.1]heptane-7-carboxylate using 1,8-diazabicyclo[5.4.0]undec-7-ene in accordance with the method described by Wolkoff, supra. The desired product, 2-(2-(3-pyridyl)vinyl-7-azabicyclo[2.2.1] heptane, can be obtained by treatment of the latter compound with refluxing aqueous hydrochloric acid.

The manner in which certain aryl-substituted olefinic amine compounds possessing a 2-azabicyclo[2.2.1]heptane moiety are synthesized can vary. In one synthetic approach, ethyl 3-aza-3-((4-toluenesulfonyl)bicyclo[2.2.1]hept-5-ene-2-carboxylate, synthesized according to the method of Hamley et al., *Synlett.* 29 (1991), can be reduced to 2-aza-3-(hydroxymethyl)-2-((4-toluenesulfonyl)bicyclo[2.2.1]hept-5-ene using an excess of diisobutyllithium hydride at 0° C. Reduction of the olefin can be accomplished by various methods known to those skilled in the art, such as hydrogenation over a palladium catalyst, to give 2-aza-3-(hydroxymethyl)-2-((4-toluenesulfonyl)bicyclo[2.2.1]heptane. This alcohol can then be converted to 2-aza-3-(iodomethyl)-2-((4-toluenesulfonyl)bicyclo[2.2.1]heptane using diethyl azodicarboxylate, triphenylphosphine and iodine as described previously. Conversion of the latter alkyl iodide to the Grignard reagent, followed by reaction with pyridine 3-carboxaldehyde, affords 3-(2-(3-pyridyl)-2-hydroxyethyl)-2-aza-2-((4-toluenesulfonyl)bicyclo[2.2.1]heptane. Treatment of the latter compound with methanesulfonyl chloride yields the O-mesylate, which can in turn be eliminated to give 3-(2-(3-pyridyl)vinyl)-2-aza-2-((4-toluenesulfonyl)bicyclo[2.2.1]heptane using 1,8-diazabicyclo [5.4.0]undec-7-ene in accordance with the methods described above. Finally, the desired product, 3-(2-(3-pyridyl)vinyl)-2-azabicyclo[2.2.1]heptane, can be obtained by treatment of the aforementioned N-tosylate with sodium naphthylide according to the procedure of Ji et al., *J. Am. Chem. Soc.* 89:5311 (1967).

The manner in which certain aryl ethynyl azabicyclic compounds possessing a 1-azabicyclo[3.3.0]octane moiety are synthesized can vary. In one approach, compounds such as 5-(2-(5-azabicyclo[3.3.0]octyl)ethynyl)pyridine can be prepared by the addition of the lithium salt of 3-ethynylpyridine to 1,2,3,5,6,7-hexahydropyrrolizinium perchlorate at low temperature (−78° C.). The required starting material, 3-ethynylpyridine can be prepared from pyridine-3-carboxaldehyde by treatment with tetrabromomethane and triphenylphosphine, followed by treatment of the resulting 1,1-dibromo-2-(3-pyridyl)ethylene with n-butyllithium at low temperature (−78° C.) according to synthetic methods set forth in U.S. Pat. No. 5,616,707 to Crooks et al. Alternatively, 3-ethynylpyridine can be prepare by the copper (I) iodide and palladium-catalyzed alkynylation of 3-bromopyridine with 2-methyl-3-butyn-2-ol, followed by heating the resulting intermediate with a strong base such as sodium hydride, according to synthetic methods similar to those described by Cosford et al., *J Med. Chem.* 39: 3235 (1996), and Bleicher et al., *J. Org. Chem.*, 63: 1109 (1998). The aforementioned 1,2,3,5,6,7-hexahydropyrrolizinium perchlorate can be prepared according to the general synthetic methods of Miyano et al., *Synthesis,* 701 (1978) and Miyano et al, *J Het. Chem.* 19:1465 (1982).

In another synthetic approach, compounds such as 5-(2-(5-azabicyclo[3.3.0]octyl)ethynyl)pyridine can be prepared by the palladium-catalyzed Sonagashira coupling (Thorand et al, *J. Org. Chem.* 63: 8551 (1998)) of 3-bromopyridine and 1-aza-5-ethynylbicyclo[3.3.0]octane. Catalysts, such as copper (I) iodide and bis(triphenylphosphine)palladium dichloride, and triethylamine as a base in dichloromethane as a solvent can be used. The required synthetic intermediate, 1-aza-5-ethynylbicyclo[3.3.0]octane can be prepared by the addition of 1,2,3,5,6,7-hexahydropyrrolizinium perchlorate to a solution of ethynylmagnesium bromide in tetrahydrofuran according to synthetic methods set forth in U.S. Pat. No. 5,733,912 to Wasicak et al.

The manner in which certain aryl vinyl azabicyclic compounds of the present invention are synthesized can vary. In one approach, compounds such as (E)-5-(2-(3-pyridyl)vinyl)-1-azabicyclo[3.3.0]octane can be synthesized by the palladium-catalyzed Heck reaction of 3-bromopyridine and 1-aza-5-vinylbicyclo[3.3.0]octane. Typically, procedures similar to those set forth in Frank et al., *J. Org. Chem.* 43: 2947 (1978) and Malek et al., *J. Org. Chem.* 47: 5395 (1982) can be used. Catalysts such as palladium (II) acetate and ligands such as tri-o-tolylphosphine can be used in a solvent such as acetonitrile using triethylamine as a base. The aforementioned 1-aza-5-vinylbicyclo[3.3.0]octane can be prepared by the addition of 1,2,3,5,6,7-hexahydropyrroliziniun perchlorate to a solution of vinylmagnesium bromide (commercially available from Aldrich Chemical Company).

In a similar approach, cis-olefinic compounds such as (Z)-5-(2-(3-pyridyl)vinyl)-1-azabicyclo[3.3.0]octane can be prepared by the selective hydrogenation of the corresponding alkynyl compound, 5-(2-(5-azabicyclo[3.3.0]octyl)ethynyl)pyridine using Lindlar's catalyst (palladium on calcium carbonate) as described by Lindlar et al. *Org. Syn.* 46: 89 (1966).

Related compounds such as 5-(2-(3-pyridyl)ethyl)-1-azabicyclo[3.3.0]octane can be prepared by hydrogenation of the corresponding ethynyl or vinyl compound, namely 5-(2-(5-azabicyclo[3.3.0]octyl)ethynyl)pyridine or 5-(2-(5-azabicyclo[3.3.0]octyl)vinyl)pyridine, using a catalyst such as palladium on carbon.

The manner in which certain 5-substituted-pyridyl ethynyl azabicyclic compounds possessing a 1-azabicyclo[3.3.0] octane moiety are synthesized can vary. In one approach, compounds such as 5-(2-(5-azabicyclo[3.3.0]octyl)ethynyl)-3-cyclopentyloxypyridine can be prepared by the palladium-catalyzed Sonagashira coupling (Thorand et al, supra) of 5-cyclopentyloxy-3-bromopyridine and 1-aza-5-ethynylbicyclo[3.3.0]octane. Catalysts, such as copper (I) iodide and bis(triphenylphosphine)palladium dichloride, and triethylamine as a base in dichloromethane as a solvent can be used. The required synthetic intermediate, 1-aza-5-ethynylbicyclo[3.3.0]octane, can be prepared as described above. The aforementioned 5-cyclopentyloxy-3-bromopyridine can be prepared by heating 3,5-dibromopyridine with cyclopentanol in the presence of sodium in a solvent such as N-methyl-pyrrolidinone, using copper powder as a catalyst. Techniques similar to those reported by Comins et al., *J. Org. Chem.* 55: 69 (1990) and Den Hertog et al., *Recl. Trav. Chim. Pays-Bas.* 74: 1171 (1955) can be used.

The manner in which certain 5-substituted-pyridyl vinyl azabicyclic compounds of the present invention are synthesized can vary. In one approach, compounds such as (E)-5-(2-(5-azabicyclo[3.3.0]octyl)vinyl)-3-cyclopentyloxypyridine can be synthesized by the palladium catalyzed Heck reaction of 5-cyclopentyloxy-3-bromopyridine and 1-aza-5-vinylbicyclo[3.3.0]octane, as previously described. The aforementioned 1-aza-5-vinylbicyclo[3.3.0]octane can be prepared by the addition of 1,2,3,5,6,7-hexahydropyrroliziniun perchlorate to a solution of vinylmagnesium bromide, as described above.

The manner in which certain pyrimidinyl ethynyl azabicyclic compounds possessing a 1-azabicyclo[3.3.0]octane moiety are synthesized can vary. In one approach, compounds such as 5-(2-(5-azabicyclo[3.3.0]octyl)ethynyl)pyrimidine can be prepared by the palladium-catalyzed Sonagashira coupling of 5-bromopyrimidine (commercially available from Aldrich Chemical Company) and 1-aza-5-ethynylbicyclo[3.3.0]octane. Catalysts, such as copper (I) iodide and bis(triphenylphosphine)palladium dichloride, and triethylamine as a base in dichloromethane as a solvent can be used. The required synthetic intermediate, 1-aza-5-ethynylbicyclo[3.3.0]octane can be prepared according to the synthetic methods described previously.

The manner in which certain pyrimidinyl vinyl azabicyclic compounds of the present invention are synthesized can vary. In one approach, compounds such as (E)-5-(2-(5-azabicyclo[3.3.0]octyl)vinyl)pyrimidine can be synthesized by the palladium-catalyzed Heck reaction of 1-aza-5-vinylbicyclo[3.3.0]octane and 5-bromopyrimidine. The aforementioned 1-aza-5-vinylbicyclo[3.3.0]octane can be prepared by the addition of 1,2,3,5,6,7-hexahydropyrroliziniun perchlorate to a solution vinylmagnesium bromide, as described above.

Related compounds such as (E)-5-(2-(5-azabicyclo[3.3.0] octyl)ethyl)pyrimidine can be prepared by catalytic hydrogenation of (E)-5-(2-(5-azabicyclo[3.3.0]octyl)vinyl)pyrimidine or 5-(2-(5-azabicyclo[3.3.0]octyl)ethynyl) pyrimidine, using a catalyst such as palladium on carbon.

The present invention relates to a method for providing prevention of a condition or disorder to a subject susceptible to such a condition or disorder, and for providing treatment to a subject suffering therefrom. For example, the method comprises administering to a patient an amount of a compound effective for providing some degree of prevention of the progression of a CNS disorder (i.e., provide protective effects), amelioration of the symptoms of a CNS disorder, and amelioration of the recurrence of a CNS disorder. The method involves administering an effective amount of a compound selected from the general formulae, which are set forth hereinbefore. The present invention relates to a pharmaceutical composition incorporating a compound selected from the general formulae, which are set forth hereinbefore. Optically active compounds can be employed as racemic mixtures or as pure enantiomers. The compounds can be employed in a free base form or in a salt form (e.g., as pharmaceutically acceptable salts). Examples of suitable pharmaceutically acceptable salts include inorganic acid addition salts such as hydrochloride, hydrobromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with an acidic amino acid such as aspartate and glutamate; alkali metal salts such as sodium and potassium; alkaline earth metal salts such as magnesium and calcium; ammonium salt; organic basic salts such as trimethylamine, triethylamine, pyridine, picoline, dieyclohexylamine, and N,N'-dibenzylethylenediamine; and salts with a basic amino acid such as lysine and arginine. The salts may be in some cases hydrates or ethanol solvates. Representative salts are provided as described in U.S. Pat. No. 5,597,919 to Dull et al., U.S. Pat. No. 5,616,716 to Dull et al. and U.S. Pat. No. 5,663,356 to Ruecroft et al., the disclosures of which are incorporated herein by reference in their entirety.

Compounds of the present invention are useful for treating those types of conditions and disorders for which other types of nicotinic compounds have been proposed as therapeutics. See, for example, Williams et al., *Drug News Perspec.* 7(4):205 (1994), Arneric et al., *CNS Drug Rev.* 1(1):1 (1995), Arneric et al., *Exp. Opin. Invest. Drugs* 5(1):79 (1996), Bencherif et al., *J. Pharmacol. Exp. Ther.* 279:1413 (1996), Lippiello et al., *J. Pharmacol. Exp. Ther.* 279:1422 (1996), Damaj et al., *J. Pharmacol. Exp. Ther.* 291:390 (1999); Chiari et al., *Anesthesiology* 91:1447 (1999); Lavand'homme and Eisenbach, *Anesthesiology* 91:1455 (1999); Holladay et al., *J. Med. Chem* 40(28):4169

(1997), Bannon et al., *Science* 279:77 (1998), PCT WO 94/08992, PCT WO 96/31475, and U.S. Pat. No. 5,583,140 to Bencherif et al., U.S. Pat. No. 5,597,919 to Dull et al., and U.S. Pat. No. 5,604,231 to Smith et al., the disclosures of which are incorporated herein by reference in their entirety. Compounds of the present invention can be used as analgesics, to treat ulcerative colitis, inflammatory and autoimmune diseases (e.g., arthritis, cholangitis, stomatitis, pouchitis, viral pneumonitis), to treat a variety of neurodegenerative diseases, and to treat convulsions such as those that are symptomatic of epilepsy. CNS disorders which can be treated in accordance with the present invention include pre-senile dementia (early onset Alzheimer's disease), senile dementia (dementia of the Alzheimer's type), HIV-dementia, multiple cerebral infarcts, Parkinsonism including Parkinson's disease, Pick's disease, Huntington's chorea, tardive dyskinesia, hyperkinesia, mania, attention deficit disorder, anxiety, depression, mild cognitive impairment, dyslexia, schizophrenia and Tourette's syndrome. Compounds of the present invention also can be used to treat conditions such as syphillis and Creutzfeld-Jakob disease. The compounds of the present invention also can be appropriately synthesized and used as or within pharmaceutical compositions that are used as diagnostic probes.

The pharmaceutical composition also can include various other components as additives or adjuncts. Exemplary pharmaceutically acceptable components or adjuncts which are employed in relevant circumstances include antioxidants, free-radical scavenging agents, peptides, growth factors, antibiotics, bacteriostatic agents, immunosuppressives, anticoagulants, buffering agents, anti-inflammatory agents, antipyretics, time-release binders, anaesthetics, steroids, vitamins, minerals and corticosteroids. Such components can provide additional therapeutic benefit, act to affect the therapeutic action of the pharmaceutical composition, or act towards preventing any potential side effects which may be imposed as a result of administration of the pharmaceutical composition. In certain circumstances, a compound of the present invention can be employed as part of a pharmaceutical composition with other compounds intended to prevent or treat a particular disorder.

The manner in which the compounds are administered can vary. The compounds can be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); intrathecally; intracerebroventricularly; or transdermally (e.g., using a transdermal patch). Although it is possible to administer the compounds in the form of a bulk active chemical, it is preferred to present each compound in the form of a pharmaceutical composition or formulation for efficient and effective administration. Exemplary methods for administering such compounds will be apparent to the skilled artisan. For example, the compounds can be administered in the form of a tablet, a hard gelatin capsule or as a time-release capsule. As another example, the compounds can be delivered transdermally using the types of patch technologies available from Novartis and Alza Corporation. The administration of the pharmaceutical compositions of the present invention can be intermittent or at a gradual, continuous, constant or controlled rate to a warm-blooded animal (e.g., a mammal such as a mouse, rat, cat, rabbit, dog, pig, cow, or monkey), but advantageously is administered preferably to a human being. In addition, the time of day and the number of times per day that the pharmaceutical formulation is administered can vary. Preferable administration is such that the active ingredients of the pharmaceutical formulation interact with receptor sites within the body of the subject that affect the functioning of the CNS. More specifically, in treating a CNS disorder, preferable administration is designed to optimize the effect upon those relevant receptor subtypes that have an effect upon the functioning of the CNS, while minimizing the effects upon muscle-type receptor subtypes. Other suitable methods for administering the compounds of the present invention are described in U.S. Pat. No. 5,604,231 to Smith et al.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder. Thus, when treating a CNS disorder, an effective amount of compound is an amount sufficient to pass across the blood-brain barrier of the subject, to bind to relevant receptor sites in the brain of the subject and to activate relevant nicotinic receptor subtypes (e.g., provide neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the recurrence of the symptoms of the disorder.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to activate relevant receptors to effect neurotransmitter (e.g., dopamine) release, but the amount should be insufficient to induce effects on skeletal muscles and ganglia to any significant degree. The effective dose of compounds will of course differ from patient to patient, but in general includes amounts starting where CNS effects or other desired therapeutic effects occur but below the amount where muscular effects are observed.

The compounds useful according to the method of the present invention have the ability to pass across the blood-brain barrier of the patient. As such, these compounds have the ability to enter the central nervous system of the patient. The log P values of typical compounds, which are useful in carrying out the present invention, are generally greater than about −0.5, often are greater than about 0, and frequently are greater than about 0.5. The log P values of such typical compounds generally are less than, about 3, often are less than about 2, and frequently are less than about 1. Log P values provide a measure of the ability of a compound to pass across a diffusion barrier, such as a biological membrane, including the blood brain barrier. See, for example, Hansch et al., *J. Med. Chem.* 11:1 (1968).

The compounds useful according to the method of the present invention have the ability to bind to, and in most circumstances, cause activation of, nicotinic dopaminergic receptors of the brain of the patient. As such, these compounds have the ability to express nicotinic pharmacology and, in particular, to act as nicotinic agonists. The receptor binding constants of typical compounds useful in carrying out the present invention generally exceed about 0.1 nM, often exceed about 1 nM, and frequently exceed about 10 nM. The receptor binding constants of certain compounds are less than about 100 µM, often are less than about 10 µM and frequently are less than about 5 µM; and of preferred compounds generally are less than about 2.5 µM, sometimes are less than about 1 µM, and can be less than about 100 nM. Receptor binding constants provide a measure of the ability of the compound to bind to half of the relevant receptor sites of certain brain cells of the patient. See, for example, Cheng et al., *Biochem. Pharmacol.* 22:3099 (1973).

The compounds useful according to the method of the present invention have the ability to demonstrate a nicotinic function by effectively activating neurotransmitter secretion from nerve ending preparations (i.e., synaptosomes). As such, these compounds have the ability to activate relevant neurons to release or secrete acetylcholine, dopamine, and other neurotransmitters. Generally, typical compounds useful in carrying out the present invention provide for the activation of dopamine secretion in amounts of at least one third, typically at least about 10 times less, frequently at least about 100 times less, and sometimes at least about 1,000 times less than those required for activation of muscle-type nicotinic receptors. Certain compounds of the present invention can provide secretion of dopamine in an amount which is comparable to that elicited by an equal molar amount of (S)-(−)-nicotine.

The compounds of the present invention, when employed in effective amounts in accordance with the method of the present invention, are selective to certain relevant nicotinic receptors, but do not cause significant activation of receptors associated with undesirable side effects at concentrations at least greater than those required for activation of dopamine release. By this is meant that a particular dose of compound resulting in prevention and/or treatment of a CNS disorder is essentially ineffective in eliciting activation of certain ganglionic-type nicotinic receptors at concentration higher than 5 times, preferably higher than 100 times, and more preferably higher than 1,000 times than those required for activation of dopamine release. This selectivity of certain compounds of the present invention against those ganglionic-type receptors responsible for cardiovascular side effects is demonstrated by a lack of the ability of those compounds to activate nicotinic function of adrenal chromaffin tissue at concentrations greater than those required for activation of dopamine release.

Compounds of the present invention, when employed in effective amounts in accordance with the method of the present invention, are effective towards providing some degree of prevention of the progression of CNS disorders, amelioration of the symptoms of CNS disorders, and amelioration to some degree of the recurrence of CNS disorders. However, such effective amounts of those compounds are not sufficient to elicit any appreciable side effects, as demonstrated by increased effects relating to skeletal muscle. As such, administration of certain compounds of the present invention provides a therapeutic window in which treatment of certain CNS disorders is provided and certain side effects are avoided. That is, an effective dose of a compound of the present invention is sufficient to provide the desired effects upon the CNS but is insufficient (i.e., is not at a high enough level) to provide undesirable side effects. Preferably, effective administration of a compound of the present invention resulting in treatment of CNS disorders occurs upon administration of less than ⅕, and often less than ¹/₁₀, that amount sufficient to cause certain side effects to any significant degree.

The pharmaceutical compositions of the present invention can be employed to prevent or treat certain other conditions, diseases and disorders. Exemplary of such diseases and disorders include inflammatory bowel disease, pouchitis, acute cholangitis, aphthous stomatitis, arthritis (e.g., rheumatoid arthritis and osteoarthritis), neurodegenerative diseases, cachexia secondary to infection (e.g., as occurs in AIDS, AIDS-related complex and neoplasia), as well as those indications set forth in PCT WO 98/25619. The pharmaceutical compositions of the present invention can be employed in order to ameliorate many of the symptoms associated with those conditions, diseases and disorders. Thus, pharmaceutical compositions of the present invention can be used in treating genetic diseases and disorders, in treating auto-immune disorders such as lupus, as anti-infectious agents (e.g., for treating bacterial, fungal and viral infections, as well as the effects, such as sepsis, of other types of toxins), as anti-inflammatory agents (e.g., for treating acute cholangitis, aphthous stomatitis, asthma, and ulcerative colitis), and as inhibitors of cytokine release (e.g., as is desirable in the treatment of cachexia, inflammation, neurodegenerative diseases, viral infection, and neoplasia). The compounds of the present invention can also be used as adjunct therapy in combination with existing therapies in the management of the aforementioned types of diseases and disorders. In such situations, preferable administration is such that the active ingredients of the pharmaceutical formulation act to optimize effects upon abnormal cytokine production, while minimizing effects upon receptor subtypes such as those that are associated with muscle and ganglia. Preferable administration is such that active ingredients interact with regions where cytokine production is affected or occurs. For the treatment of such conditions or disorders, compounds of the present invention are very potent (i.e., affect cytokine production and/or secretion at very low concentrations) and are very efficacious (i.e., significantly inhibit cytokine production and/or secretion to a relatively high degree).

Most preferably, effective doses are at very low concentrations, where maximal effects are observed to occur. Concentrations, determined as the amount of compound per volume of relevant tissue, typically provide a measure of the degree to which that compound affects cytokine production. Typically, the effective dose of compounds generally requires administering the compound in an amount of less than 5 mg/kg of patient weight. Often, the compounds of the present invention are administered in an amount from less than about 1 mg/kg patient weight and usually less than about 100 µg/kg of patient weight, but frequently between about 10 µg to less than 100 µg/kg of patient weight. For compounds of the present invention that do not induce effects on muscle-type nicotinic receptors at low concentrations, the effective dose is less than 5 mg/kg of patient weight; often such compounds are administered in an amount from 50 µg to less than 5 mg/kg of patient weight. The foregoing effective doses typically represent that amount administered as a single dose, or as one or more doses administered over a 24-hour period.

For human patients, the effective dose of typical compounds generally requires administering the compound in an amount of at least about 1, often at least about 10, and frequently at least about 25 µg/24 hr/patient. For human patients, the effective dose of typical compounds requires administering the compound which generally does not exceed about 1, often does not exceed about 0.75, often does not exceed about 0.5, and frequently does not exceed about 0.2 mg/24 hr/patient. In addition, administration of the effective dose is such that the concentration of the compound within the plasma of the patient normally does not exceed 500 pg/mL, often does not exceed 300 pg/mL, and frequently does not exceed 100 pg/mL.

When employed in such a manner, compounds of the present invention are dose dependent, and, as such, cause inhibition of cytokine production and/or secretion when employed at low concentrations but do not exhibit those inhibiting effects at higher concentrations. Compounds of the present invention exhibit inhibitory effects upon cytokine production and/or secretion when employed in amounts less than those amounts necessary to elicit activation of relevant nicotinic receptor subtypes to any significant degree.

The following examples are provided to illustrate the present invention and should not be construed as limiting the scope thereof. In these examples, all parts and percentages are by weight, unless otherwise noted. Reaction yields are reported in mole percentages.

EXAMPLES

Assays

Determination of Binding to Relevant Receptor Sites

Binding of the compounds to relevant receptor sites was determined in accordance with the techniques described in U.S. Pat. No. 5,597,919 to Dull et al. Inhibition constants ($K_i$ values), reported in nM, were calculated from the $IC_{50}$ values using the method of Cheng et al., *Biochem. Pharmacol.* 22:3099 (1973). Low binding constants indicate that the compounds of the present invention exhibit good high affinity binding to certain CNS nicotinic receptors.

Example 1

Sample No. 1 is (2S)-(2E)-2-(3-prop-1-(3-pyridyl)-1-enyl)pyrrolidine hemigalactarate (or (S)-(E)-3-(3-pyrrolidin-2-yl-prop-1-enyl)pyridine hemigalactarate), which was prepared in accordance with the following techniques:

(2S)-N-(tert-Butoxycarbonyl)-2-(hydroxymethyl) pyrrolidine

Under a nitrogen atmosphere, an ice-cold stirring solution of (2S)-2-pyrrolidinemethanol (3.00 g, 29.7 mmol, Aldrich Chemical Company), triethylamine (4.3 mL, 3.12 g, 30.9 mmol) in dry dichloromethane (50 mL) was treated in portions over 10 min with di-tert-butyl dicarbonate (7.11 g, 32.6 mmol). The solution was stirred and allowed to warm to ambient temperature overnight. Saturated aqueous NaHCO$_3$ solution (25 mL) was added, and the mixture was extracted with CHCl$_3$ (3×50 mL). The combined extracts were dried (K$_2$CO$_3$), filtered and concentrated under vacuum producing 5.50 g (92.1%) of a thick, colorless syrup.

(2S)-N-(tert-Butoxycarbonyl)-2-(iodomethyl)pyrrolidine

Under a nitrogen atmosphere, a solution of diethyl azodicarboxylate (4.699 g, 26.98 mmol) in dry tetrahydrofuran (THF) (15 mL) was added drop-wise to an ice-cold stirring solution of (2S)-N-(tert-butoxycarbonyl)-2-(hydroxymethyl)pyrrolidine (5.37 g, 26.7 mmol), iodine (3.42 g, 13.5 mmol) and triphenylphosphine (7.069 g, 26.95 mmol) in dry THF (50 mL). The mixture was stirred and allowed to warm to ambient temperature overnight. The mixture was concentrated on a rotary evaporator and then the residue was stirred with 5% aqueous Na$_2$S$_2$O$_3$ (50 mL). After stirring for 30 min, the mixture was extracted with dichloromethane (4×25 mL). The combined dichloromethane extracts were dried (Na$_2$SO$_4$), filtered and concentrated. The residue was repeatedly crystallized (three to four times) from dry ether and finally from heptane to give 3.20 g (38.6%) of product.

(2S)-N-(tert-Butoxycarbonyl)-2-allylpyrrolidine

Under a nitrogen atmosphere, a solution of vinylmagnesium bromide, 1.0 M in tetrahydrofuran (2.0 mL, 2.0 mmol) was slowly added to a suspension of copper(I) iodide (244.9 mg, 1.28 mmol) in dry diethyl ether (10 mL) at −78° C. Upon completion of the addition, the mixture was warmed to −36° C. for 5 min and was then cooled to −78° C. A solution of (2S)-N-(tert-butoxycarbonyl)-2-(iodomethyl) pyrrolidine (200.0 mg, 0.64 mmol) in dry diethyl ether (5 mL) was added over a period of 10 min. The reaction mixture was warmed to −36° C. and was stirred at −36° C. for 6 h. The resulting dark mixture was treated with saturated aqueous NH$_4$Cl solution (5 mL) and was stirred while warming to ambient temperature. The reaction mixture was extracted with diethyl ether (4×10 mL). The combined ether extracts were dried (Na$_2$SO$_4$), filtered and concentrated under vacuum to yield a pale-yellow oil (200 mg). The product was purified by column chromatography, eluting with hexane:ethyl acetate (1:1). Fractions containing the product were combined and concentrated under vacuum to afford 100 mg (73.6%) of an oil.

(2S)-(2E)-N-(tert-Butoxycarbonyl)-2-(3-prop-1-(3-pyridyl)-1-enyl)pyrrolidine

A thick-walled glass pressure tube was charged with (2S)-N-(tert-butoxycarbonyl)-2-allylpyrrolidine (100.0 mg, 0.47 mmol), 3-bromopyridine (112.3 mg, 0.71 mmol), palladium(II) acetate (10.63 mg, 0.047 mmol), tri-o-tolylphosphine (14.42 mg, 0.074 mmol), triethylamine (1.0 mL, 7.2 mmol) and acetonitrile (10 mL). The tube was sealed and the reaction mixture was stirred and heated at 110–120° C. for 8 h. After cooling, the tube contents were added to a stirring, saturated aqueous NaHCO$_3$ solution. The mixture was extracted with CHCl$_3$ (4×20 mL). The combined CHCl$_3$ extracts were dried (K$_2$CO$_3$), filtered and concentrated under vacuum to give a thick, dark syrup (500 mg). The product was purified by column chromatography, eluting with a gradient of ethyl acetate:hexane (20:80 to 50:50). Fractions containing the product were combined and concentrated under vacuum to give 75.0 mg (54.9%) of an oil.

(2S)-(2E)-2-(3-Prop-1-(3-pyridyl)-1-enyl)pyrrolidine

Under a nitrogen atmosphere, an ice-cold stirring solution of (2S)-(2E)-N-(tert-butoxycarbonyl)-2-(3-prop-1-(3-pyridyl)-1-enyl)pyrrolidine (50.0 mg, 0.17 mmol) in anisole (1 mL) was treated with trifluoroacetic acid (1 mL). After stirring for 30 min, the solution was treated with saturated aqueous NaHCO$_3$ solution, saturated with solid NaCl, and extracted with CHCl$_3$ (5×10 mL). The combined CHCl$_3$ extracts were dried (K$_2$CO$_3$), filtered and concentrated on a rotary evaporator to give a thick, dark syrup. The product was purified by column chromatography, eluting with a gradient of chloroform:methanol (up to 9:1), containing 1% Et₃N. Selected fractions were combined and concentrated under vacuum to give 20.0 mg (61.3%) of a pale, light-yellow oil.

(2S)-(2E)-2-(3-Prop-1-(3-pyridyl)-1-enyl)pyrrolidine hemigalactarate

Galactaric acid (10.0 mg, 0.048 mmol) was added to a solution of (2S)-(2E)-2-(3-prop-1-(3-pyridyl)-1-enyl)pyrrolidine (18.0 mg, 0.096 mmol) in absolute ethanol (1 mL). The mixture was heated at 60° C. and sonicated. Water (2–3 drops) was added, and the process was repeated 3–4 times producing a clear solution. The solution was filtered and concentrated; ethanol (2 mL) was added to the residue and removed by rotary evaporation. The resulting solid was dissolved in a minimum amount of ethanol and dry diethyl ether was added, producing a cloudy solution. After standing 2 days at ambient temperature, the resulting solid was filtered and washed with ether to give 16.6 mg (59.1%) of a pale, light-yellow solid, mp 138–141° C.

Sample No. 1 exhibits a $K_i$ of 472 nM. The low binding constant indicates that the compound exhibits good high-affinity binding to certain CNS nicotinic receptors.

Example 2

Sample No. 2 is (S)-(E)-3(2-pyrrolidin-2-ylvinyl)pyridine hemigalactarate, which was prepared in accordance with the following techniques:

(S)-N-tert-Butoxycarbonyl-2-formylpyrrolidine

Pyridinium chlorochromate (3.26 g, 15.2 mmol) was added to a solution of (2S)-N-(tert-butoxycarbonyl)-2-(hydroxymethyl)pyrrolidine (2.77 g, 13.8 mmol) in dichloromethane (50 mL) and the mixture was stirred at room temperature for 12 h. The solvent was removed on a rotary evaporator to give a dark brown gum, which was chromatographed, using ethyl acetate:hexane (1:1, v/v) as eluant. Selected fractions containing the product were combined and concentrated on a rotary evaporator to give 1.45 g (52.9% yield) of a colorless oil.

(S)-(N-tert-Butoxycarbonyl)-2-vinylpyrrolidine

The title compound was prepared according to the procedure of Corey et al., *J. Amer. Chem. Soc.* 104: 4724 (1982). Thus, n-butyllithium (0.70 mL, 2.5 M solution in hexane) was added to a stirred ice-cold solution of methyl triphenylphosphonium bromide (634.7 mg, 1.776 mmol) in anhydrous diethyl ether (10 mL). The mixture was allowed to warm to room temperature, stirred for 3 h, and was then added dropwise via a cannula to a cold (−78° C.) solution of (2S)-N-(tert-butoxycarbonyl)-2-formylpyrrolidine (350 mg, 1.77 mmol) in anhydrous diethyl ether (10 mL) under a nitrogen atmosphere. The reaction mixture was allowed to warm to room temperature and stirred for 16 h. Saturated aqueous NH₄Cl solution (2 mL) was added, the mixture stirred for 10 min and extracted with ethyl acetate (3×15 mL). The combined ethyl acetate extracts were dried (K₂CO₃), filtered and concentrated on a rotary evaporator to give a viscous brown oil, which was chromatographed, using ethyl acetate:hexane (1:9, v/v) as eluant. Selected fractions containing the product were combined and concentrated under vacuum to afford 310 mg (89.5% yield) of a colorless oil.

(S)-(E)-N-(tert-Butoxycarbonyl)-2-(2-(3-pyridyl)vinyl)pyrrolidine

In a sealed pressure tube under a nitrogen atmosphere, 3-bromopyridine (264.67 mg, 1.675 mmol), (2S)-N-tert-butoxycarbonyl-2-vinylpyrrolidine (300 mg, 1.52 mmol), tri-o-tolylphosphine (46.82 mg, 0.153 mmol), palladium(II) acetate (34.53 mg, 0.15 mmol), triethylamine (2 mL) and acetonitrile (20 mL) were stirred at 90° C. for 14 h. The tube was cooled and the contents were slowly poured into a stirred saturated aqueous NaHCO₃ solution (20 mL) and extracted with chloroform (4×20 mL). The combined chloroform extracts were dried (K₂CO₃), filtered and concentrated under vacuum to give 500 mg of a viscous dark oil, which was chromatographed with an ethyl acetate:hexane gradient (1:4 to 1:1, v/v) as eluant. Selected fractions containing the product were combined and concentrated on a rotary evaporator to give 310 mg (84.0% yield) of pale-yellow oil.

(S)-(E)-3-(2-Pyrrolidin-2-ylvinyl)pyridine

Under a nitrogen atmosphere, trifluoroacetic acid (1 mL) was added dropwise to a stirred ice-cold solution of (2S)-N-(tert-butoxycarbonyl)-2-(2-(3-pyridyl)vinyl)pyrrolidine (280 mg, 1.02 mmol) in anisole (2 mL). The reaction mixture was allowed to warm to room temperature, stirred for 16 h, then neutralized with saturated aqueous NaHCO₃ solution, saturated with solid NaCl and extracted with chloroform (5×10 mL). The combined chloroform extracts were dried (K₂CO₃), filtered and concentrated on a rotary evaporator to give a viscous dark oil, which was chromatographed with chloroform:methanol (9:1, v/v) and 1% triethylamine as eluant. Selected fractions containing the product were combined and concentrated on a rotary evaporator to give 130 mg (73.1% yield) of a colorless oil.

(S)-(E)-3-(2-Pyrrolidin-2-ylvinyl)pyridine hemigalactarate

To a stirred solution of (2S)-3-(2-pyrrolidin-2-ylvinyl)pyridine (120 mg, 0.689 mmol) in ethanol (2 mL), galactaric acid (72.4 mg, 0.344 mmol) was added. The mixture was heated at 70° C., sonicated and then water (1–2 drops) was added; this process was repeated until most of the solid dissolved. The remaining insoluble material was removed by filtration. To the filtrate anhydrous diethyl ether was added dropwise until it became cloudy. After 16 h at 4° C. a precipitate was formed; this was filtered and vacuum dried to give 120 mg (61.9% yield) of product as a light brown solid.

Sample No. 2 exhibits a $K_i$ of 306 nM. The low binding constant indicates that the compound exhibits good high-affinity binding to certain CNS nicotinic receptors.

Example 3

Sample No. 3 is (S)-5-(2-Pyrrolidin-2-ylethynyl)pyrimidine, which was prepared according to the following techniques:

(2S)-N-(tert-Butoxycarbonyl)-2-ethynylpyrrolidine

A solution of (2S)-N-(tert-butoxycarbonyl)-2-formylpyrrolidine (4.0 g, 20 mmole), carbon tetrabromide (6.67 g, 20.1 mmole) and triphenylphosphine (5.26 g, 20.1 mmole) in methylene chloride (100 mL) was stirred at ambient temperature under a nitrogen atmosphere for 24 hours. The mixture was concentrated, then purified by chromatography, using (1:1) ethyl acetate:hexane as eluant to provide the desired product as an oil. The product was dissolved in dry tetrahydrofuran (50 mL) and cooled to −78° C. A solution of n-butyllithium (50.25 mL, 20.1 mmole, 2.5 M solution in hexanes) was added and the mixture was stirred at −78° C. for 1 h. The material was quenched with water (20 mL) and extracted with ethyl acetate (3×50 mL). The combined extracts were dried ($K_2CO_3$), concentrated and purified by chromatography, using (1:1) ethyl acetate:hexane as eluant to provide (3.10 g, 91%) of a colorless oil.

(S)-N-(tert-Butoxycarbonyl)-2-(2-(5-pyrimidinyl) ethynyl)pyrrolidine

Triethylamine (10 mL) was degassed by bubbling argon over a period of 30 min. (S)-N-tert-Butoxycarbonyl-2-ethynylpyrrolidine (0.300 g, 5.12 mmol), tetrakis(triphenylphosphine)palladium (0.180 g, 0.1 mmol), palladium(II) acetate (0.0346 g, 0.10 mmol), copper (I) iodide (6.25 mg, 0.033 mmol) and 5-bromo-pyrimidine (0.4867 g, 3.07 mmol) were added. The mixture was heated at 110° C. for 9 h, then cooled to room temperature and concentrated by rotary evaporation. The residue was dissolved in chloroform (50 mL) and the organic phase washed with water (25 mL), saturated aqueous $NaHCO_3$ solution (3×20 mL) and water (25 mL), then dried ($MgSO_4$), filtered and concentrated by rotary evaporation. The crude product was purified by column chromatography, eluting with ethyl acetate/hexane (1/1, v/v). Selected fractions containing the product were concentrated via rotary evaporation to give 0.310 g (74%) of a yellow oil.

(S)-5-(Pyrrolidin-2-ylethynyl)pyrimidine

An ice-cold stirred solution (S)-N-tert-butoxycarbonyl-2-(3-pyrimidinyl)ethynyl-1-pyrrolidine (310 mg, 2.3 mmol) in ethyl acetate (25 mL) was treated with hydrochloric acid (1 mL). The mixture was stirred for 10 min at 0–5° C., then for 3 h at room temperature. The layers were separated and the pH of the aqueous portion was brought to 12 with 1N NaOH. The aqueous phase was extracted with ethyl acetate (2×25 mL). The combined organic phases were washed with brine (5 mL), then dried ($MgSO_4$), filtered and concentrated by rotary evaporation. The crude product was purified by column chromatography on silica gel, eluting with chloroform/methanol (90/10, v/v). Selected fractions containing the product were concentrated via rotary evaporation to give 0.046 g of a yellow oil.

Sample No. 3 exhibits a $K_i$ of 46 nM. The low binding constant indicates that the compound exhibits good high-affinity binding to certain CNS nicotinic receptors.

Example 4

Sample No. 4 is (R)-5-(2-Pyrrolidin-2-ylethynyl)pyrimidine, which was prepared according to the methods described for Example 3 using the corresponding (R)-N-(tert-butoxycarbonyl)-2-formylpyrrolidine enantiomer.

Sample No. 4 exhibits a $K_i$ of 342 nM. The low binding constant indicates that the compound exhibits good high-affinity binding to certain CNS nicotinic receptors.

Example 5

Sample No. 5 is (S)-5-(2-Pyrrolidin-2-ylethynyl)pyridine, which was prepared according to the following techniques:

(S)-N-(tert-Butoxycarbonyl)-2-(2-(3-pyridyl)ethynyl)pyrrolidine

Triethylamine (10 mL) was degassed by bubbling argon over a period of 30 min. (S)-N-(tert-butoxycarbonyl)-2-ethynylpyrrolidine (1.00 g, 5.12 mmol), tetrakis(triphenylphosphine)palladium (0.296 g, 0.256 mmol), palladium (II) acetate (0.0575 g, 0.256 mmol), copper (I) iodide (16.2 mg, 0.085 mmol) and 5-bromopyridine (2.43 g, 15.4 mmol) were added. The mixture was heated at 60° C. for 24 h, then cooled to room temperature and concentrated by rotary evaporation. The residue was dissolved in chloroform (50 mL) and the organic phase washed sequentially with water (25 mL), saturated aqueous $NaHCO_3$ solution (3×20 mL) and water (25 mL). The solution was then dried ($MgSO_4$), filtered and concentrated by rotary evaporation. The crude product was purified by column chromatography on silica gel, eluting with ethyl acetate/hexane (1/1, v/v). Selected fractions containing the product were concentrated via rotary evaporation to give 1.00 g (71%) of a yellow oil.

(S)-2-(2-(3-Pyridyl)ethynyl)pyrrolidine

An ice-cold stirred solution (S)-N-(tert-butoxycarbonyl)-2-(2-(3-pyridyl)ethynyl)pyrrolidine (300 mg, 1.10 mmol) in ethyl acetate (25 mL) was treated with concentrated hydrochloric acid (1 mL). The mixture was stirred for 10 min at 0–5° C., then for 3 h at room temperature. The layers were separated and the pH of the aqueous portion was brought to 12 with 1N NaOH. The aqueous phase was extracted with ethyl acetate (2×25 mL). The combined organic phases were washed with brine (5 mL), then dried ($MgSO_4$), filtered and concentrated by rotary evaporation. The crude product was purified by column chromatography on silica gel, eluting with chloroform/methanol (90/10, v/v). Selected fractions containing the product were concentrated via rotary evaporation to give 0.120 g of a yellow oil.

Sample No. 5 exhibits a $K_i$ of 12 nM. The low binding constant indicates that the compound exhibits good high-affinity binding to certain CNS nicotinic receptors.

Example 6

Sample No. 6 is (R)-5-(2-Pyrrolidin-2-ylethynyl)pyridine, which was prepared according to the methods described for Example 5 using the corresponding (R)-N-(tert-butoxycarbonyl)-2-formylpyrrolidine and 3-bromopyridine.

Sample No. 6 exhibits a $K_i$ of 450 nM. The low binding constant indicates that the compound exhibits good high-affinity binding to certain CNS nicotinic receptors.

Example 7

Sample No. 7 is (S)-3-isopropoxy-5-(pyrrolidin-2-ylethynyl)pyridine hemigalactarate, which was prepared in accordance with the following techniques:

3-Bromo-5-isopropoxypyridine

This product was prepared using the procedure described in patent WO 0075110.

(S)-N-(tert-Butoxycarbonyl)-2-ethynyl-1-pyrrolidine

This product was prepared using the procedure described by Trybulski et al., *J. Med. Chem.* 33(12):3190 (1990).

(S)-N-(tert-Butoxycarbonyl)-2-(5-isopropoxy-3-pyridyl)ethynyl-1-pyrrolidine

Diisopropylethylamine (10 mL) was degassed by bubbling argon over a period of 30 min. (S)-N-tert-Butoxycarbonyl-2-ethynyl-1-pyrrolidine (0.391 g, 2 mmol), tetrakis(triphenylphosphine)palladium (0.115 g, 0.1 mmol), palladium(II) acetate (0.022 g, 0.1 mmol), copper (I) iodide (6.25 mg, 0.033 mmol) and 3-bromo-5-isopropoxypyridine (0.87 g, 4 mmol) were added. The mixture was heated at 110° C. for 15 h, then cooled to room temperature and concentrated by rotary evaporation. The residue was dissolved in ethyl acetate (50 mL) and the organic phase washed with water (25 mL), saturated aqueous $NaHCO_3$ solution (2×25 mL) and water (25 mL), then dried ($MgSO_4$), filtered and concentrated by rotary evaporation. The crude product was purified by column chromatography, eluting with ethyl acetate/cyclohexane (20/80, v/v). Selected fractions containing the product were concentrated via rotary evaporation and joined to the product of another similar experiment to give 1.1 g of crude product, which was purified by column chromatography, eluting with ethyl acetate/cyclohexane (20/80, v/v). Selected fractions containing the product were concentrated via rotary evaporation to give 0.66 g (17%) of an orange oil.

(S)-3-Isopropoxy-5-(pyrrolidin-2-ylethynyl)pyridine hemigalactarate

An ice-cold stirred solution of (S)-N-(tert-butoxycarbonyl)-2-(5-isopropoxy-3-pyridyl)ethynyl-1-pyrrolidine (660 mg, 1.8 mmol) in dichloromethane (12.5 mL) was treated with trifluoroacetic acid (2.8 mL). The mixture was stirred for 20 min at 0–5° C., then for 3 h at room temperature and concentrated by rotary evaporation. To the oily residue was added water (20 mL) and the pH was brought to 12 with 1N NaOH. The aqueous phase was extracted with ethyl acetate (2×25 mL). The combined organic phases were washed with brine (5 mL), then dried ($MgSO_4$), filtered and concentrated by rotary evaporation. The crude product was purified by column chromatography, eluting with dichloromethane/methanol (90/10, v/v). Selected fractions containing the product were concentrated via rotary evaporation to give 0.34 g of a yellow oil. To a solution of this oil in a mixture of methanol (9 mL) and water (1 mL) was added galactaric acid (155 mg, 0.73 mmol). The mixture was stirred and heated until complete dissolution of the galactaric acid, then was cooled to room temperature and concentrated by rotary evaporation to give an oil, which was triturated in a mixture of ethanol (1 mL) and isopropyl acetate (6 mL). The resulting solid was filtered, washed with isopropyl acetate, then diisopropyl ether (2×5 mL) and dried under vacuum at 50° C. to afford 380 mg (63%) of an off-white solid.

Sample No. 7 exhibits a $K_i$ of 2 nM. The low binding constant indicates that the compound exhibits good high-affinity binding to certain CNS nicotinic receptors.

Example 8

Sample No. 8 is (S)-3-phenyl-5-(pyrrolidin-2-ylethynyl)pyridine hemigalactarate, which was prepared in accordance with the following techniques:

3-Bromo-5-phenylpyridine

This product was prepared using the procedure described in patent WO 9837071.

(S)-N-(tert-Butoxycarbonyl)-2-(5-phenyl-3-pyridyl)ethynyl-1-pyrrolidine

Triethylamine (15 mL) was degassed by bubbling argon over a period of 30 min. (S)-N-(tert-Butoxycarbonyl)-2-ethynyl-1-pyrrolidine (0.781 g, 4 mmol), crude (90% purity) 3-bromo-5-phenylpyridine (1.97 g, 4 mmol), tetrakis(triphenylphosphine) palladium (0.231 g, 0.2 mmol), palladium (II) acetate (0.045 g, 0.2 mmol) and copper (I) iodide (13.3 mg, 0.07 mmol) were added. The mixture was heated under reflux for 3 h, then cooled to room temperature and concentrated by rotary evaporation. The residue was dissolved in ethyl acetate (50 mL) and the organic phase washed with water (2×25 mL), saturated aqueous $NaHCO_3$ solution (2×25 mL) and water (2×25 mL), then dried ($MgSO_4$), filtered and concentrated by rotary evaporation. The crude product was purified by column chromatography, eluting with ethyl acetate/cyclohexane (20/80, v/v). Selected fractions containing the product were concentrated via rotary evaporation to give 0.7 g (50%) of an orange oil.

(S)-3-Phenyl-5-(pyrrolidin-2-ylethynyl)pyridine hemigalactarate

An ice-cold stirred solution of (S)-N-(tert-butoxycarbonyl)-2-(5-phenyl-3-pyridyl)ethynyl-1-pyrrolidine (0.7 g, 2 mmol) in dichloromethane (15.5 mL) was treated with trifluoroacetic acid (3.1 mL). The mixture was stirred for 30 min at 0–5° C., then for 3 h at room temperature and concentrated by rotary evaporation. To the oily residue was added water (25 mL) and the pH was brought to 12 with 1N NaOH. The aqueous phase was extracted with dichloromethane (3×30 mL). The combined organic phases were washed with brine (25 mL), then dried ($MgSO_4$), filtered and concentrated by rotary evaporation. The crude product was purified by column chromatography, eluting with dichloromethane/methanol (90/10, v/v). Selected fractions containing the product were concentrated via rotary evaporation to give 0.34 g of a yellow oil. To a solution of this oil in a mixture of methanol (9 mL) and water (1 mL) was added galactaric acid (141 mg). The mixture was stirred and heated until complete dissolution of the galactaric acid and then concentrated by rotary evaporation to give an oil, which was triturated in a mixture of ethanol (1 mL) and isopropyl acetate (5 mL). The resulting solid was filtered, washed with isopropyl acetate, then diisopropyl ether and dried under vacuum at 40° C. to give 0.4 g (56%) of an off-white solid.

Sample No. 8 exhibits a $K_i$ of 56 nM. The low binding constant indicates that the compound exhibits good high-affinity binding to certain CNS nicotinic receptors.

Example 9

Sample No. 9 is (S)-3-(phenoxyphenyl)-5-(pyrrolidin-2-ylethynyl)pyridine hemigalactarate, which was prepared in accordance with the following techniques:

3-Bromo-5-(phenoxyphenyl)pyridine

Under a nitrogen atmosphere, a mixture of 3,5-dibromopyridine (5.16 g, 21.8 mmol), water (36.5 mL), toluene (145 mL), ethanol (36.5 mL), 4-phenoxyphenylboronic acid (5.00 g, 23.3 mmol), sodium carbonate (4.9 g, 47 mmol) and tetrakis(triphenylphosphine)palladium (1.25 g, 1.04 mmol) was stirred and heated under reflux for 5 h. After cooling to room temperature, water (150 mL) was added and the aqueous phase separated and extracted with ethyl acetate (3×100 mL). The combined organic phases were washed with water (50 mL), then dried ($MgSO_4$), treated with 3S Black (decolorizing charcoal), filtered, and concentrated by rotary evaporation. The residue was purified by column chromatography, eluting with cyclohexane/ethyl acetate (90/10, v/v) to give 2.3 g (32%) of a white solid, mp 109° C.

(S)-N-(tert-Butoxycarbonyl)-2-(5-(phenoxyphenyl)-3-pyridyl)ethynyl-1-pyrrolidine Triethylamine (15 mL) was degassed by bubbling argon over a period of 30 min. (S)-N-tert-(Butoxycarbonyl)-2-ethynyl-1-pyrrolidine (0.781 g, 4 mmol), 3-bromo-5-phenoxypyridine (2.31 g, 8 mmol), tetrakis(triphenylphosphine) palladium (0.231 g, 0.2 mmol), palladium(II) acetate (0.045 g, 0.2 mmol) and copper (I) iodide (13.3 mg, 0.07 mmol) were added. The mixture was heated under reflux for 3 h, then cooled to room temperature and concentrated by rotary evaporation. The residue was dissolved in ethyl acetate (50 mL) and the organic phase washed with water (2×25 mL), saturated bicarbonate aqueous solution (2×25 mL) and water (25 mL), then dried ($MgSO_4$), filtered and concentrated by rotary evaporation. The crude product was purified by column chromatography, eluting with ethyl acetate/cyclohexane (20/80, v/v). Selected fractions containing the product were concentrated via rotary evaporation to give 0.9 g (51%) of an orange oil.

(S)-3-(Phenoxyphenyl)-5-(pyrrolidin-2-ylethynyl)pyridine hemigalactarate

An ice-cold stirred solution of (S)-N-(tert-butoxycarbonyl)-2-(5-(phenoxyphenyl)-3-pyridyl)ethynyl-1-pyrrolidine (900 mg, 2 mmol) in dichloromethane (16 mL) was treated with trifluoroacetic acid (3.2 mL). The mixture was stirred for 30 min at 0–5° C., then for 3 h at room temperature, and then it was concentrated on a rotary evaporator. To the oily residue was added water (25 mL) and the pH was brought to 12 with 1N NaOH. The aqueous phase was extracted with dichloromethane (3×25 mL). The combined organic phases were washed with brine (5 mL), then dried ($MgSO_4$), filtered and concentrated by rotary evaporation. The crude product was purified by column chromatography, eluting with dichloromethane/methanol (90/10, v/v). Selected fractions containing the product were concentrated via rotary evaporation to give 0.5 g of a yellow oil. To a solution of the residue in a mixture of methanol (9 mL) and water (2 mL) was added galactaric acid (154 mg, 0.73 mmol). The mixture was stirred and heated until complete dissolution of the galactaric acid, then was cooled to room temperature and concentrated by rotary evaporation to give an oil, which was triturated in a mixture of ethanol (2 mL) and isopropyl acetate (9 mL). The resulting solid was filtered, washed with isopropyl acetate, then diisopropyl ether and dried under vacuum at 40° C. to afford 580 mg (64%) of an off-white solid.

Sample No. 9 exhibits a $K_i$ of 530 nM. The low binding constant indicates that the compound exhibits good high-affinity binding to certain CNS nicotinic receptors.

Example 10

Sample No. 10 is (S)-3-(4-methoxyphenoxy)-5-(pyrrolidin-2-ylethynyl)pyridine hemigalactarate, which was prepared in accordance with the following techniques:

3-Bromo-5-(4-methoxyphenoxy)pyridine

Under an argon atmosphere, a solution of 4-methoxyphenol (15.7 g, 0.126 mol) in dimethylformamide (50 mL) was added slowly to a stirred suspension sodium hydride (3.6 g of a 80% suspension in mineral oil, 0.125 mol) in dimethylformamide (100 mL) at 3–7° C. The ice-bath was removed and the resulting mixture was stirred for 2 h at room temperature. A solution of 3,5-dibromopyridine (20 g, 0.083 mol) in dimethylformamide (120 mL) was added to the mixture, which was then heated to 100° C. for 36 h, then cooled to room temperature and poured into a mixture of water (500 mL) and ethyl acetate (500 mL). The aqueous phase was separated and extracted with ethyl acetate (2×100 mL). The combined organic phases were washed with water (3×100 mL) and then brine (100 mL), then dried ($MgSO_4$), filtered and concentrated by rotary evaporation to give 22.5 g of an orange oil, which was purified by column chromatography, with cyclohexane/ethyl acetate (95/5, v/v) as eluant. Selected fractions containing the product were concentrated via rotary evaporation to give 18.8 g (81%) of a colorless oil.

(S)-N-(tert-Butoxycarbonyl)-2-(5-(4-methoxyphenoxy)-3-pyridyl)ethynyl-1-pyrrolidine Triethylamine (25 mL) was degassed by bubbling argon over a period of 30 min. (S)-N-tert-Butoxycarbonyl-2-ethynyl-1-pyrrolidine (0.977 g, 5 mmol), 3-bromo-5-(4-methoxyphenoxy)pyridine (2.1 g, 7.5 mmol), tetrakis(triphenylphosphine) palladium (0.289 g, 0.25 mmol), palladium (II) acetate (0.056 g, 0.25 mmol) and copper (I) iodide (20 mg, 0.11 mmol) were added. The mixture was heated under reflux for 3 h, then was cooled to room temperature and concentrated by rotary evaporation. The residue was dissolved in ethyl acetate (50 mL) and the organic phase washed with water (2×25 mL), saturated aqueous $NaHCO_3$ solution (2×25 mL) and water (25 mL), then dried ($MgSO_4$), filtered and concentrated by rotary evaporation. The crude product was purified by column chromatography, eluting with ethyl acetate/cyclohexane (20/80, v/v). Selected fractions containing the product were concentrated via rotary evaporation to give 0.95 (48%) of an orange oil.

(S)-3-(4-Methoxyphenoxy)-5-(pyrrolidin-2-ylethynyl)pyridine hemigalactarate

An ice-cold stirred solution of (S)-N-(tert-butoxycarbonyl)-2-(5-(4-methoxyphenoxy)-3-pyridyl)ethynyl-1-pyrrolidine (0.95 g, 2.41 mmol) in dichloromethane (19 mL) was treated with trifluoroacetic acid (3.7 mL). The mixture was stirred for 30 min at 0–5° C., then for 3 h at room temperature, and then it was concentrated on a rotary evaporator. To the oily residue was added water (10 mL) and the pH was brought to 12 with 1N NaOH. The aqueous phase was extracted with dichloromethane (3×25 mL). The combined organic phases were washed with brine (5 mL), then dried (MgSO$_4$), filtered and concentrated by rotary evaporation. The crude product was purified by column chromatography, eluting with dichloromethane/methanol (90/10, v/v). Selected fractions containing the product were concentrated via rotary evaporation to give 0.45 g of a yellow oil. To a solution of the residue in a mixture of methanol (10 mL) and water (2 mL) was added galactaric acid (157 mg, 0.75 mmol). The mixture was stirred and heated until complete dissolution of the galactaric acid, then was cooled to room temperature and concentrated by rotary evaporation to give an oil, which was triturated in a mixture of ethanol (2 mL) and isopropyl acetate (7 mL). The resulting solid was filtered, washed with isopropyl acetate and dried under vacuum at 40° C. to afford 490 mg (51%) of an off-white solid.

Sample No. 10 exhibits a K$_i$ of 33 nM. The low binding constant indicates that the compound exhibits good high-affinity binding to certain CNS nicotinic receptors.

Example 11

Sample No. 11 is (S)-3-(4-hydroxyphenoxy)-5-(pyrrolidin-2-ylethynyl)pyridine, which was prepared in accordance with the following techniques:

(S)-3-(4-Hydroxyphenoxy)-5-(pyrrolidin-2-ylethynyl)pyridine

A cold (−10° C.), stirred solution of (S)-N-(tert-butoxycarbonyl)-2-(5-(4-methoxyphenoxy)-3-pyridyl)ethynyl-1-pyrrolidine (1.1 g, 2.79 mmol) in dichloromethane (25 mL) was treated with 1M solution of boron tribromide in dichloromethane (8.4 mL, 8.4 mmol). The mixture was stirred for 3 h at −10° C., then for 20 h at room temperature, and then water (20 mL) was added and the pH brought to 7–8 with 1N NaOH. The aqueous phase was extracted with dichloromethane (3×50 mL). The combined organic phases were washed with water (50 mL), then dried (MgSO$_4$), filtered and concentrated by rotary evaporation. The crude product was purified by column chromatography, eluting with dichloromethane/methanol (90/10, v/v). Selected fractions containing the product were concentrated via rotary evaporation to give 0.4 g of solid, which was recrystallized in isopropanol (3 mL) affording 250 mg (32%) of an off-white solid (m.p. 164° C.).

Sample No. 11 exhibits a K$_i$ of 2 nM. The low binding constant indicates that the compound exhibits good high-affinity binding to certain CNS nicotinic receptors.

Example 12

Sample No. 12 is (S)-3-cyclopentyloxy-5-(pyrrolidin-2-ylethynyl)pyridine, which was prepared in accordance with the following techniques:

3-Bromo-5-cyclopentyloxypyridine

To a mixture of 5-bromo-3-pyridinol (5.22 g, 30 mmol), toluene (180 mL), triphenylphosphine (11.8 g, 45 mmol) and cyclopentanol (4.12 mL, 45 mmol) was slowly added diethyl azodicarboxylate (7.1 mL, 45 mmol). The mixture was heated at 90° C. for 20 h, then cooled to room temperature, washed with water (3×100 mL) and then brine (100 mL), then dried (MgSO$_4$), filtered and concentrated by rotary evaporation. The crude oil was purified by column chromatography, eluting with ethyl acetate/cyclohexane (10/90, v/v). Selected fractions containing the product were concentrated via rotary evaporation to give 6.5 g (89%) of an orange oil.

(S)-N-(tert-Butoxycarbonyl)-2-(5-cyclopentyloxy-3-pyridyl)ethynyl-1-pyrrolidine

Triethylamine (25 mL) was degassed by bubbling argon over a period of 30 min. (S)-N-tert-(Butoxycarbonyl)-2-ethynyl-1-pyrrolidine (0.976 g, 5.0 mmol), 3-bromo-5-cyclopentyloxypyridine (1.82 g, 7.5 mmol), tetrakis(triphenylphosphine)palladium (0.289 g, 0.25 mmol), palladium (II) acetate (0.056 g, 0.25 mmol) and copper (I) iodide (21 mg, 0.11 mmol) were added. The mixture was heated under reflux for 3 h, then cooled to room temperature and concentrated by rotary evaporation. The residue was dissolved in ethyl acetate (100 mL) and the organic phase washed with water (3×50 mL), saturated aqueous NaHCO$_3$ solution (2×50 mL), water (50 mL) and then brine (50 mL), then dried (MgSO$_4$), filtered and concentrated by rotary evaporation. The crude product was purified by column chromatography, eluting with ethyl acetate/cyclohexane (20/80, v/v). Selected fractions containing the product were concentrated via rotary evaporation to give 0.8 g (45%) of an orange oil.

(S)-3-Cyclopentyloxy-5-(pyrrolidin-2-ylethynyl) pyridine hemigalactarate

An ice-cold stirred solution of (S)-N-(tert-butoxycarbonyl)-2-(5-cyclopentyloxy-3-pyridyl)ethynyl-1-pyrrolidine (800 mg, 2 mmol) in dichloromethane (18 mL) was treated with trifluoroacetic acid (3.46 mL). The mixture was stirred for 30 min at 0–5° C., then for 3 h at room temperature, and then it was concentrated on a rotary evaporator. To the oily residue was added water (5 mL) and the pH was brought to 8 with 1N NaOH. The aqueous phase was extracted with dichloromethane (3×25 mL). The combined organic phases were washed with brine (25 mL), then dried (MgSO$_4$), filtered and concentrated by rotary evaporation. The crude product was purified by column chromatography, eluting with dichloromethane/methanol (90/10, v/v). Selected fractions containing the product were concentrated via rotary evaporation to give 0.48 g of a yellow oil. To a solution of this oil in a mixture of methanol (7.5 mL) and water (1.5 mL) was added galactaric acid (190 mg, 0.9 mmol). The mixture was stirred and heated until complete dissolution of the galactaric acid, then was cooled to room temperature and concentrated by rotary evaporation to give an oil, which was triturated in a mixture of ethanol (1.5 mL) and isopropyl acetate (10 mL). The resulting solid was filtered, washed with isopropyl acetate and dried under vacuum at 60° C. to afford 565 mg (70%) of a beige solid.

Sample No. 12 exhibits a K$_i$ of 6 nM. The low binding constant indicates that the compound exhibits good high-affinity binding to certain CNS nicotinic receptors.

Example 13

Sample No. 13 is (S)-3-cyclohexyloxy-5-(pyrrolidin-2-ylethynyl)pyridine, which was prepared in accordance with the following techniques:

3-Bromo-5-cyclohexyloxypyridine

Under an argon atmosphere, sodium (750 mg, 31.75 mmol) was added to refluxing cyclohexanol (15 mL). The mixture was refluxed until complete consumption of sodium. The remaining cyclohexanol was removed by a stream of argon to give a white solid, which was dissolved in N-methyl-pyrrolidinone (16 mL). After addition of 3,5-dibromopyridine (3 g, 12.66 mmol), the mixture was stirred and heated at 90° C. for 1 h, then cooled to room temperature, poured into cold (5° C.) water (60 mL), and extracted with diethyl ether (3×50 mL). The combined organic phases were washed with water (25 mL) and then brine (25 mL), then dried ($MgSO_4$), filtered and concentrated by rotary evaporation to give 6.2 g of an orange oil, which was purified by column chromatography, eluting with cyclohexane/ethyl acetate (95/5, v/v). Selected fractions containing the product were concentrated via rotary evaporation to give 1.6 g (50%) of a light-yellow oil.

(S)-N-(tert-Butoxycarbonyl)-2-(5-cyclohexyloxy-3-pyridyl)ethynyl-1-pyrrolidine Triethylamine (25 mL) was degassed by bubbling argon over a period of 30 min. (S)-N-tert-(Butoxycarbonyl)-2-ethynyl-1-pyrrolidine (0.976 g, 5 mmol), 3-bromo-5-cyclohexyloxypyridine (1.92 g, 7.5 mmol), tetrakis(triphenylphosphine)palladium (0.289 g, 0.25 mmol), palladium (II) acetate (0.056 g, 0.25 mmol) and copper (I) iodide (21 mg, 0.11 mmol) were added. The mixture was heated under reflux for 3 h, then cooled to room temperature and concentrated by rotary evaporation. The residue was dissolved in ethyl acetate (100 mL) and the organic phase washed with water (2×50 mL), saturated aqueous $NaHCO_3$ solution (50 mL), water (2×50 mL) and brine (50 mL), then dried ($MgSO_4$), filtered and concentrated by rotary evaporation. The crude product was purified by column chromatography, eluting with ethyl acetate/cyclohexane (20/80, v/v). Selected fractions containing the product were concentrated via rotary evaporation to give 1.2 g (65%) of a yellow oil.

(S)-3-Cyclohexyloxy-5-(pyrrolidin-2-ylethynyl)pyridine hemigalactarate

An ice-cold stirred solution of (S)-N-(tert-butoxycarbonyl)-2-(5-cyclohexyloxy-3-pyridyl)ethynyl-1-pyrrolidine (1.2 g, 3.24 mmol) in dichloromethane (12.5 mL) was treated with trifluoroacetic acid (2.5 mL). The mixture was stirred for 30 min at 0–5° C., then for 3 h at room temperature, and then it was concentrated on a rotary evaporator. To the oily residue was added water (10 mL) and the pH was brought to 12 with 1N NaOH. The aqueous phase was extracted with dichloromethane (3×50 mL). The combined organic phases were washed with brine (50 mL), then dried ($MgSO_4$), filtered and concentrated by rotary evaporation. The crude product was purified by column chromatography, eluting with dichloromethane/methanol (95/5, v/v). Selected fractions containing the product were concentrated via rotary evaporation to give 0.6 g of a yellow oil. To a solution of this oil in a mixture of methanol (10 mL) and water (2 mL) was added galactaric acid (233 mg, 1.11 mmol). The mixture was stirred and heated at 50° C. until complete dissolution of the galactaric acid, then cooled to room temperature and concentrated by rotary evaporation to give an oil, which was triturated in a mixture of ethanol (2 mL) and isopropyl acetate (10 mL). The resulting solid was filtered, washed with isopropyl acetate, then diisopropyloxide, and dried under vacuum at 60° C. to afford 0.66 g (54%) of a beige solid.

Sample No. 13 exhibits a $K_i$ of 90 nM. The low binding constant indicates that the compound exhibits good high-affinity binding to certain CNS nicotinic receptors.

Example 14

Sample No. 14 is (S)-3-(4-(pyrrolidine-1-sulfonyl)phenoxy)-5-(pyrrolidin-2-ylethynyl)pyridine hemigalactarate, which was prepared in accordance with the following techniques:

3-Bromo-5-(4-(pyrrolidine-1-sulfonyl)phenoxy)pyridine

A mixture of 5-bromo-3-pyridinol (2.61 g, 15 mmol), dimethylacetamide (50 mL), 1-((4-fluorophenyl)sulfonyl) pyrrolidine (5.8 g, 25 mmol) and potassium carbonate (4.1 g, 30 mmol) was heated at 120° C. for 18 h, then cooled to room temperature and concentrated by rotary evaporation. The residue was dissolved in ethyl acetate (200 mL) and the organic phase washed with water (3×100 mL) and brine (100 mL), then dried ($MgSO_4$), filtered and concentrated by rotary evaporation. The crude product was purified by column chromatography, eluting with ethyl acetate/cyclohexane (20/80, v/v). Selected fractions containing the product were concentrated via rotary evaporation to give 3.4 g (59%) of a red solid (m.p. 148° C.)

(S)-N-(tert-Butoxycarbonyl)-2-(5-(4-(pyrrolidine-1-sulfonyl)phenoxy)-3-pyridyl)ethynyl-1-pyrrolidine Triethylamine (25 mL) was degassed by bubbling argon over a period of 30 min. (S)-N-(tert-Butoxycarbonyl)-2-ethynyl-1-pyrrolidine (0.977 g, 5 mmol), 3-bromo-5-[4-(pyrrolidine-1-sulfonyl)phenoxy]pyridine (2.87 g, 7.5 mmol), tetrakis(triphenylphosphine)palladium (0.289 g, 0.25 mmol), palladium(II) acetate (0.056 g, 0.25 mmol) and copper (I) iodide (21 mg, 0.11 mmol) were added. The mixture was heated under reflux for 3 h, then cooled to room temperature and concentrated by rotary evaporation. The residue was dissolved in ethyl acetate (100 mL) and the organic phase washed with water (2×50 mL), saturated aqueous $NaHCO_3$ solution (2×50 mL), water (2×50 mL) and brine (50 mL), then dried ($MgSO_4$), filtered and concentrated by rotary evaporation. The crude product was purified by column chromatography, eluting with ethyl acetate/cyclohexane (30/70, v/v). Selected fractions containing the product were concentrated via rotary evaporation to give 2 g (80%) of an orange oil.

(S)-3-(4-(Pyrrolidine-1-sulfonyl)phenoxy)-5-(pyrrolidin-2-ylethynyl)pyridine hemigalactarate An ice-cold stirred solution of (S)-N-(tert-butoxycarbonyl)-2-(5-(4-(pyrrolidine-1-sulfonyl)phenoxy)-3-pyridyl) ethynyl-1-pyrrolidine (2 g, 4.02 mmol) in dichloromethane (15.5 mL) was treated with trifluoroacetic acid (3.1 mL). The mixture was stirred for 30 min at 0–5° C., then for 3 h at room temperature, and then it was concentrated on a rotary evaporator. To the oily residue was added water (10 mL) and the pH was adjusted to 12 with 1N NaOH. The aqueous phase was extracted with dichloromethane (3×50 mL). The combined organic phases were washed with water (50 mL), then dried (MgSO$_4$), filtered and concentrated by rotary evaporation. The crude product was purified by column chromatography, eluting with dichloromethane/methanol (95/5, v/v). Selected fractions containing the product were concentrated via rotary evaporation to give 1.1 g of a yellow oil. To a solution of this oil in a mixture of methanol (10 mL) and water (2 mL) was added galactaric acid (280 mg, 1.38 mmol). The mixture was stirred and heated at 50° C. until complete dissolution of the galactaric acid, then cooled to room temperature and concentrated by rotary evaporation to give an oil, which was triturated in a mixture of ethanol (2 mL) and isopropyl acetate (10 mL). The resulting solid was filtered, washed with isopropyl acetate, then diisopropyl ether, and dried under vacuum at 60° C. to afford 1.2 g (59%) of a beige solid.

Sample No. 14 exhibits a $K_i$ of 100 nM. The low binding constant indicates that the compound exhibits good high-affinity binding to certain CNS nicotinic receptors.

Example 15

Sample No. 15 is (S)-3-(3-pyridyloxy)-5-(pyrrolidin-2-ylethynyl)pyridine hemigalactarate, which was prepared in accordance with the following techniques:

3-Bromo-5-(3-pyridyloxy)pyridine

To a solution of 3-pyridinol (4.32 g, 45 mmol) in dimethylformamide (50 mL) was added sodium hydride (1.35 g of a 80% suspension in mineral oil, 45 mmol). The mixture was stirred for 1 h at room temperature and 3,5-dibromopyridine (5.92 g, 25 mmol) was added. The mixture was heated for 20 h at 130° C., then cooled to room temperature and poured into water (300 mL). The aqueous phase was extracted with diethyl ether (3×100 mL) and the organic phase was washed with water (2×100 mL) and brine (100 mL), then dried (MgSO$_4$), filtered and concentrated by rotary evaporation. The crude product was purified by column chromatography, eluting with ethyl acetate/cyclohexane (30/70, v/v). Selected fractions containing the product were concentrated via rotary evaporation to give 3.5 g (56%) of a yellow oil.

(S)-N-(tert-butoxycarbonyl)-2-(5-(3-pyridyloxy))-3-pyridyl)ethynyl-1-pyrrolidine Triethylamine (25 mL) was degassed by bubbling argon over a period of 30 min. (S)-N-(tert-butoxycarbonyl)-2-ethynyl-1-pyrrolidine (0.977 g, 5 mmol), 3-bromo-5-(3-pyridyloxy)pyridine (1.88 g, 7.5 mmol), tetrakis(triphenylphosphine)palladium (0.289 g, 0.25 mmol), palladium (II) acetate (0.056 g, 0.25 mmol) and copper (I) iodide (21 mg, 0.11 mmol) were added. The mixture was heated under reflux for 3 h, then cooled to room temperature and concentrated by rotary evaporation. The residue was dissolved in ethyl acetate (100 mL) and the organic phase washed with water (2×50 mL), saturated aqueous NaHCO$_3$ solution (50 mL), water (50 mL) and brine (50 mL), then dried (MgSO$_4$), filtered and concentrated by rotary evaporation. The crude product was purified by column chromatography, eluting with ethyl acetate/cyclohexane (40/60, v/v). Selected fractions containing the product were concentrated via rotary evaporation to give 1.5 g (82%) of an orange oil.

(S)-3-(3-Pyridyloxy)-5-(pyrrolidin-2-ylethynyl)pyridine hemigalactarate

An ice-cold stirred solution of (S)-N-(tert-butoxycarbonyl)-2-(5-(3-pyridyloxy))-3-pyridyl)ethynyl-1-pyrrolidine (1.5 g, 4.1 mmol) in dichloromethane (16 mL) was treated with trifluoroacetic acid (3.2 mL). The mixture was stirred for 30 min at 0–5° C., then for 3 h at room temperature, and then it was concentrated on a rotary evaporator. To the oily residue was added water (10 mL) and the pH was brought to 12 with 1N NaOH. The aqueous phase was extracted with dichloromethane (3 times 50 mL). The combined organic phases were washed with water (50 mL) and then brine (50 mL), then dried (MgSO$_4$), filtered and concentrated by rotary evaporation. The crude product was purified by column chromatography, eluting with dichloromethane/methanol (95/5, v/v). Selected fractions containing the product were concentrated via rotary evaporation to give 620 mg of a yellow oil. To a solution of this oil in a mixture of methanol (10 mL) and water (2 mL) was added galactaric acid (245 mg, 1.17 mmol). The mixture was stirred and heated at 50° C. until complete dissolution of the galactaric acid, then cooled to room temperature and concentrated by rotary evaporation to give an oil, which was triturated in a mixture of ethanol (2 mL) and isopropyl acetate (10 mL). The resulting solid was filtered, washed with isopropyl acetate (2 times 5 mL), then diisopropyl oxide, and dried under vacuum at 60° C. to afford 0.75 g (49%) of a cream solid.

Sample No. 15 exhibits a $K_i$ of 13 nM. The low binding constant indicates that the compound exhibits good high-affinity binding to certain CNS nicotinic receptors.

Example 16

Sample No. 16 is (S)-3-(pyrrolidin-2-ylethynyl)-5-(tetrahydropyran-4-yloxy)pyridine hemigalactarate, which was prepared in accordance with the following techniques:

3-Bromo-5-(tetrahydropyran-4-yloxy)pyridine

To a mixture of 5-bromo-3-pyridinol (5.22 g, 30 mmol), toluene (150 mL), triphenylphosphine (11.8 g, 45 mmol) and tetrahydropyran-4-ol (4.7 g, 45 mmol) was slowly added diethyl azodicarboxylate (7.1 mL, 45 mmol). The mixture was heated at reflux for 20 h, then cooled to room temperature, washed with water (3×100 mL) and then brine (100 mL), then dried (MgSO$_4$), filtered and concentrated by rotary evaporation. The crude oil was treated with diisopropyloxide (50 mL) and the solid thus obtained was filtered and washed with diisopropyloxide (20 mL). The combined filtrates were concentrated by rotary evaporation and purified by column chromatography on silica gel, eluting with ethyl acetate/cyclohexane (20/80, v/v). Selected fractions containing the product were concentrated via rotary evaporation to give 5 g (65%) of a yellow oil.

(S)-N-(tert-Butoxycarbonyl)-2-((5-(tetrahydropyran-4-yloxy))-3-pyridyl)ethynyl-1-pyrrolidine Triethylamine (25 mL) was degassed by bubbling argon over a period of 30 min. (S)-N-(tert-Butoxycarbonyl)-2-ethynyl-1-pyrrolidine (0.977 g, 5 mmol), 3-bromo-5-(tetrahydropyran-4-yloxy)pyridine (1.94 g, 7.5 mmol), tetrakis (triphenylphosphine)palladium (0.289 g, 0.25 mmol), palladium(II) acetate (0.056 g, 0.25 mmol) and copper (I) iodide (21 mg, 0.11 mmol) were added. The mixture was heated under reflux for 3 h, then cooled to room temperature and concentrated by rotary evaporation. The residue was dissolved in ethyl acetate (100 mL) and the organic phase washed with water (2×50 mL), saturated aqueous NaHCO$_3$ solution (50 mL), water (50 mL) and brine (50 mL), then dried (MgSO$_4$), filtered and concentrated by rotary evaporation. The crude product was purified by column chromatography, eluting with ethyl acetate/cyclohexane (40/60, v/v). Selected fractions containing the product were concentrated via rotary evaporation to give 1.5 g (81%) of an orange oil.

(S)-3-(Pyrrolidin-2-ylethynyl)-5-(tetrahydropyran-4-yloxy)pyridine hemigalactarate An ice-cold stirred solution of (S)-N-(tert-butoxycarbonyl)-2-((5-(tetrahydropyran-4-yloxy))-3-pyridyl)ethynyl-1-pyrrolidine (1.5 g, 4.0 mmol) in dichloromethane (15.5 mL) was treated with trifluoroacetic acid (3.1 mL). The mixture was stirred for 30 min at 0–5° C., then for 3 h at room temperature, and then it was concentrated on a rotary evaporator. To the oily residue was added water (10 mL) and the pH was brought to 12 with 1N NaOH. The aqueous phase was extracted with dichloromethane (3×50 mL). The combined organic phases were washed with water (50 mL) and then brine (50 mL), then dried (MgSO$_4$), filtered and concentrated by rotary evaporation. The crude product was purified by column chromatography, eluting with dichloromethane/methanol (95/5, v/v). Selected fractions containing the product were concentrated via rotary evaporation to give 0.88 g of a yellow oil. To a solution of the residue in a mixture of methanol (10 mL) and water (2 mL) was added galactaric acid (339 mg, 1.6 mmol). The mixture was stirred and heated at 50° C. until complete dissolution of the galactaric acid, then cooled to room temperature and concentrated by rotary evaporation to give an oil, which was triturated in a mixture of ethanol (3 mL) and isopropyl acetate (10 mL). The resulting solid was filtered, washed with isopropyl acetate (2×5 mL), then diisopropyl ether, and dried under vacuum at 60° C. to afford 0.98 g (64%) of a cream solid.

Sample No. 16 exhibits a K$_i$ of 7 nM. The low binding constant indicates that the compound exhibits good high-affinity binding to certain CNS nicotinic receptors.

Example 17

Sample No. 17 is (S)-3-(3,5-dihydroxy)phenoxy-5-(pyrrolidin-2-ylethynyl)pyridine, which was prepared in accordance with the following techniques:

3-Bromo-5-(3,5-Dimethoxyphenoxy)pyridine

Under an argon atmosphere, a solution of 3,5-dimethoxyphenol (6.94 g, 45 mmol) in dimethylformamide (30 mL) was added slowly to a stirred suspension of sodium hydride (1.44 g of a 75% suspension in mineral oil, 0.045 mol) in dimethylformamide (30 mL) at 0–5° C. The icebath was removed and the resulting mixture was stirred for 2.5 h at room temperature. 3,5-Dibromopyridine (7.11 g, 0.03 mol) was added to the mixture, which was then heated to 100° C. for 72 h, then the mixture was cooled to room temperature and successively washed with water (100 mL) and 5 N NaOH solution (10 mL). The mixture was extracted with diethyl ether (3×50 mL). The combined organic phases were dried (MgSO$_4$), filtered and concentrated by rotary evaporation to give 9.2 g of a white solid, which was purified by column chromatography, eluting with cyclohexane/ethyl acetate (90/10, v/v). Selected fractions containing the product were concentrated via rotary evaporation to give 2.5 g (29%) of a yellow oil.

(S)-(N-tert-Butoxycarbonyl)-2-(5-(3,5-Dimethoxy)phenoxy-3-pyridyl)ethynyl-1-pyrrolidine Triethylamine (50 mL) was degassed by bubbling argon over a period of 30 min. (S)-N-(tert-Butoxycarbonyl)-2-ethynyl-1-pyrrolidine (1.96 g, 10 mmol), 3-bromo-5-(3,5-dimethoxyphenoxy)pyridine (4.8 g, 13.93 mmol), tetrakis(triphenylphosphine)palladium (0.578 g, 0.5 mmol), palladium(II) acetate (0.112 g, 0.5 mmol) and copper (I) iodide (42 mg, 0.22 mmol) were added. The mixture was heated under reflux for 3 h, then cooled to room temperature and concentrated by rotary evaporation. The residue was dissolved in ethyl acetate (150 mL) and the organic phase washed with water (2×100 mL), saturated aqueous NaHCO$_3$ solution (100 mL) and water (100 mL), then dried (MgSO$_4$), filtered and concentrated by rotary evaporation. The crude product was purified by column chromatography, eluting with ethyl acetate/cyclohexane (20/80, v/v). Selected fractions containing the product were concentrated via rotary evaporation to give 1.6 g (38%) of an orange oil.

(S)-3-(3,5-Dihydroxy)phenoxy-5-(pyrrolidin-2-ylethynyl)pyridine

A stirred solution of (S)-N-(tert-butoxycarbonyl)-2-(5-(3,5-dimethoxy)phenoxy-3-pyridyl)ethynyl-1-pyrrolidine (1.1 g, 2.59 mmol) in dichloromethane (30 mL) was treated with 1M solution of boron tribromide in dichloromethane (10.5 mL, 10.5 mmol). The mixture was stirred for 20 h at room temperature and then concentrated by rotary evaporation. Water (10 mL) was added to the residue, then the pH was brought to 8 with saturated aqueous NaHCO$_3$ solution and the solution stirred for 30 min at room temperature. The insoluble product was separated by filtration, washed with water (3×20 mL) and dissolved in methanol-dichloromethane (20/80, v/v), then dried (MgSO$_4$, filtered and concentrated by rotary evaporation. The crude product was purified by column chromatography, eluting with dichloromethane/methanol (80/20, v/v). Selected fractions containing the product were concentrated via rotary evaporation to give a solid, which was recrystallized from isopropanol (3 mL), affording 210 mg (32%) of a beige solid (m.p. 228° C.)

Sample No. 17 exhibits a K$_i$ of 3 nM. The low binding constant indicates that the compound exhibits good high-affinity binding to certain CNS nicotinic receptors.

Example 18

Sample No. 18 is (E)-(S)-3-(4-hydroxyphenoxy)-5-(pyrrolidin-2-ylvinyl)pyridine, which was prepared in accordance with the following techniques:

(S)-3-(4-Hydroxyphenoxy)-5-(1-bromo-2-pyrrolidin-2-ylvinyl)pyridine

A stirred solution of (S)-N-(tert-butoxycarbonyl)-2-(5-(4-methoxyphenoxy)-3-pyridyl)ethynyl-1-pyrrolidine (1.1 g, 2.79 mmol) in hydrobromic acid (30 mL of a 48% aqueous solution) was heated under reflux for 10 h, then was stirred for 20 h at room temperature and concentrated by rotary evaporation. The residue was dissolved in water (10 mL) and the pH brought to 11 with 1N NaOH. The aqueous phase was extracted with dichloromethane (3×50 mL). The combined organic phases were washed with water (25 mL), then dried (MgSO$_4$), filtered and concentrated by rotary evaporation. The crude product was purified by column chromatography, eluting with dichloromethane/methanol (90/10, v/v). Selected fractions containing the product were concentrated via rotary evaporation to give 0.84 g (98%) of an orange oil.

(S)-N-(tert-Butoxycarbonyl)-(1-bromo-2-(5-(4-hydroxyphenoxy)-3-pyridyl)vinyl)-1-pyrrolidine To a stirred solution of (S)-3-(4-hydroxyphenoxy)-5-(1-bromo-2-pyrrolidin-2-ylvinyl)pyridine in dioxane (15 mL) were added water (15 mL) and sodium bicarbonate (375 mg, 4.43 mmol). The mixture was stirred until homogenous and bis(1,1-dimethylethyl)dicarbonate (488 mg, 2.21 mmol) was added. The solution was stirred at room temperature for 20 h, then brought to pH 4 by addition of 1N solution of hydrochloric acid and extracted by ethyl acetate (3×50 mL). The combined organic phases were washed with water (50 mL), then dried (MgSO$_4$), filtered and concentrated by rotary evaporation to give 1 g of an orange oil.

(E)-(S)-N-(tert-Butoxycarbonyl)-2-(5-(4-hydroxyphenoxy)-3-pyridyl)vinyl-1-pyrrolidine To a cold (−78° C.) stirred solution of (S)-N-(tert-butoxycarbonyl)-(1-bromo-2-(5-(4-hydroxyphenoxy)-3-pyridyl) vinyl)-1-pyrrolidine (1 g, 2.17 mmol) in tetrahydrofuran (20 mL) was added dropwise butyl lithium (3 mL of a 1.6 M solution in hexane, 4.77 mmol). The resulting mixture was stirred at −78° C. for 2 h, then a saturated solution of ammonium chloride was added dropwise and the pH brought to 4 by addition of a 1N solution of hydrochloric acid. The aqueous phase was extracted with ethyl acetate (3×25 mL). The combined organic phases were dried (MgSO$_4$), filtered and concentrated by rotary evaporation to give 0.8 g (96%) of an orange oil.

(E)-(S)-3-(4-Hydroxyphenoxy)-5-(pyrrolidin-2-ylvinyl)pyridine hemigalactarate

An ice-cold stirred solution of (E,S)-N-(tert-butoxycarbonyl)-2-(5-(4-hydroxyphenoxy)-3-pyridyl)vinyl-1-pyrrolidine (0.8 g, 2.09 mmol) in dichloromethane (16 mL) was treated with trifluoroacetic acid (3.22 mL). The mixture was stirred for 30 min at 0–5° C., then for 3 h at room temperature, and then it was concentrated on a rotary evaporator. To the oily residue was added water (10 mL) and the pH was brought to 8 with 1N NaOH. The aqueous phase was extracted with dichloromethane (2×75 mL). The combined organic phases were washed with water (50 mL), then dried (MgSO$_4$), filtered and concentrated by rotary evaporation. The crude product was purified by column chromatography, eluting with dichloromethane/methanol (90/10, v/v). Selected fractions containing the product were concentrated via rotary evaporation to give 0.14 g of an orange oil, which was dissolved in a mixture of methanol (5 mL) and water (1 mL) and galactaric acid (52 mg, 0.25 mmol) was added. The mixture was stirred and heated until complete dissolution of the galactaric acid, then cooled to room temperature and concentrated by rotary evaporation to give an oil, which was triturated in isopropyl acetate. The resulting solid was filtered and dried under vacuum at 40° C. to afford 178 mg (22%) of a red solid.

Sample No. 18 exhibits a K$_i$ of 20 nM. The low binding constant indicates that the compound exhibits good high-affinity binding to certain CNS nicotinic receptors.

Example 19

Sample No. 19 is (E,S)-3-cyclopentyloxy-5-(pyrrolidin-2-ylvinyl)pyridine hemigalactarate, which was prepared in accordance with the following techniques:

(S)-N-(tert-Butoxycarbonyl)-2-vinyl-1-pyrrolidine

A suspension of Lindlar catalyst (0.1 g) in a solution of (S)-N-(tert-butoxycarbonyl)-2-ethynyl-1-pyrrolidine (1.95 g, 10 mmol) in ethanol (20 mL) was shaken under a hydrogen atmosphere (1 bar) at room temperature for 3 h. The catalyst was removed by filtration and the filtrate was concentrated by rotary evaporation to give 1.98 g of a yellow oil.

(S)-N-(tert-Butoxycarbonyl)-2-(5-cyclopentyloxy-3-pyridyl)vinyl-1-pyrrolidine

A mixture of 3-bromo-5-cyclopentyloxypyridine (1.21 g, 5 mmol), (S)-N-(tert-butoxycarbonyl)-2-vinyl-1-pyrrolidine (1.25 g, 6 mmol), palladium acetate (112 mg, 0.5 mmol), diisopropylethylamine (6.9 mL, 40 mmol) and lithium chloride (636 mg, 15 mmol) in dimethylformamide (15 mL) was heated at 110° C. for 4 h, then stirred at room temperature for 2 h and concentrated by rotary evaporation. The residue was dissolved in ethyl acetate (100 mL), washed with water (3×50 mL) and then brine (50 mL), then dried (MgSO$_4$), filtered and concentrated by rotary evaporation. The crude product was purified by column chromatography, eluting with cyclohexane/ethyl acetate (80/20, v/v). Selected fractions containing the product were concentrated via rotary evaporation to give 0.7 g (39%) of an orange oil.

(E,S)-3-Cyclopentyloxy-5-(pyrrolidin-2-ylvinyl)pyridine hemigalactarate

An ice-cold stirred solution of (S)-N-(tert-butoxycarbonyl)-2-(5-cyclopentyloxy-3-pyridyl)vinyl-1-pyrrolidine (0.7 g, 1.76 mmol, 90% purity) in dichloromethane (7 mL) was treated with trifluoroacetic acid (1.36 mL). The mixture was stirred for 30 min at 0° C., then for 3 h at room temperature, and concentrated by rotary evaporation. To the oily residue was added water (5 mL) and the pH was brought to 12 with 1N NaOH. The aqueous phase was extracted with dichloromethane (3×50 mL). The combined organic phases were washed with water (50 mL) and then brine (50 mL), then dried (MgSO$_4$), filtered and concentrated by rotary evaporation. The crude product was purified by column chromatography, eluting with dichloromethane/methanol (90/10, v/v). Selected fractions containing the product were concentrated via rotary evaporation to give 0.26 g of an orange oil. To a solution of this oil in a mixture of methanol (5 mL) and water (1 mL) was added galactaric acid (105 mg, 0.5 mmol). The mixture was stirred and heated until complete dissolution of the galactaric acid, then cooled to room temperature and concentrated by rotary evaporation to give an oil, which was triturated in a mixture of ethanol (1 mL) and isopropyl acetate (5 mL). The resulting solid was filtered, washed with isopropyl acetate then diisopropyl oxide and dried under vacuum at 60° C. to afford 260 mg (40%) of a beige solid.

Sample No. 19 exhibits a K$_i$ of 51 nM. The low binding constant indicates that the compound exhibits good high-affinity binding to certain CNS nicotinic receptors.

The foregoing is illustrative of the present invention and is not to be construed as limiting thereof. The invention is defined by the following claims, with equivalents of the claims to be included therein.

What is claimed is:

1. A compound of the formula:

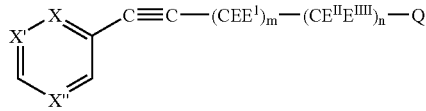

where X" is nitrogen, X is carbon bonded to a substituent species selected from the group consisting of hydrogen, alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl; arylalkyl, substituted arylalkyl, halo, —OR', —NR'R", —CF$_3$, —CN, —NO$_2$, —C$_2$R', —SR', —N$_3$, C(=O)NR'R", —NR'C(=O)R", —C(=O)R', —C(=O)OR', —OC(=O)R', —O(CR'R")$_r$C(=O)R', —O(CR'R")$_r$NR'R" —O(CR'R")$_r$NR"C(=O)R', —O(CR'R")$_r$NR"SO$_2$R', —OC(=O)NR'R", —NR'C(=O)OR", —SO$_2$R', —SO$_2$NR'R", and —NR'SO$_2$R", where R' and R" are individually hydrogen, lower alkyl, cycloalkyl, heterocyclyl, or an aromatic group-containing species selected from the group consisting of phenyl, benzyl, pyridinyl, pyrimidinyl, pyrazinyl, pyridazinyl, indolyl and quinolinyl, and r is an integer from 1 to 6, or R' and R" can together form a cycloalkyl group;

X' is COR' where R' is selected from the group consisting of aryl, substituted aryl, heteroaryl, substituted heteroaryl, non-aromatic heterocyclyl, substituted non-aromatic heterocyclyl, non-aromatic heterocyclylalkyl and substituted non-aromatic heterocyclylalkyl;

m is an integer and n is an integer such that the sum of m plus n is 0, 1, 2 or 3; E, E$^I$, E$^{II}$ and E$^{III}$ individually represent hydrogen or a suitable non-hydrogen substituent selected from the group consisting of alkyl, substituted alkyl, halo-substituted alkyl, cycloalkyl, substituted cycloalkyl, heterocyclyl, substituted heterocyclyl, aryl, substituted aryl, alkylaryl, substituted alkylaryl, arylalkyl and substituted arylalkyl; and Q is selected from:

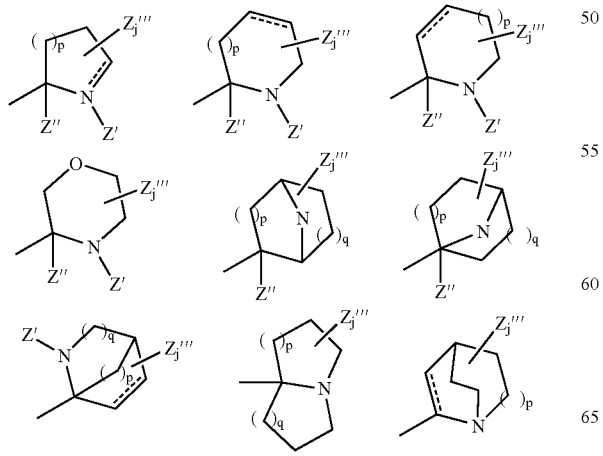

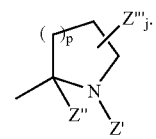

where Z' represents hydrogen or lower alkyl, acyl, alkoxycarbonyl, or aryloxycarbonyl; Z" is hydrogen or lower alkyl; and Z''' is a non-hydrogen substituent selected from the group consisting of alkyl, substituted alkyl, halo-substituted alkyl, cycloalkyl, substituted cycloalkyl, heterocyclyl, substituted heterocyclyl, aryl, substituted aryl, alkylaryl, substituted alkylaryl, arylalkyl and substituted arylalkyl; the dotted line indicates a carbon-carbon single bond or a carbon-carbon double bond; p is 0, 1 or 2; q is 0, 1, 2 or 3; and j is an integer from 0 to 3, wherein Z'''j refers to j number of Z''' substituents.

2. The compound of claim 1, wherein Q is

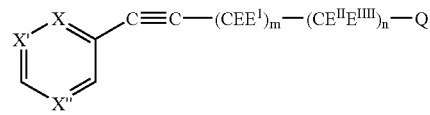

3. A pharmaceutical composition incorporating a compound of the formula:

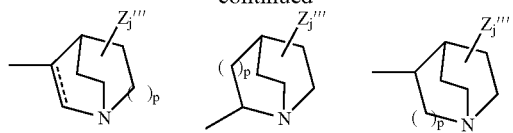

where X" is nitrogen and X is carbon bonded to a substituent species selected from the group consisting of hydrogen, alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl; arylalkyl, substituted arylalkyl, halo, —OR', —NR'R", —CF$_3$, —CN, —NO$_2$, —C$_2$R', —SR', —N$_3$, C(=O)NR'R", —NR'C(=O)R", —C(=O)R', —C(=O)OR', —OC(=O)R', —O(CR'R")$_r$C(=O)R', —O(CR'R")$_r$NR'R" —O(CR'R")$_r$NR"C(=O)R', —O(CR'R")$_r$NR"SO$_2$R', —OC(=O)NR'R", —NR'C(=O)OR", —SO$_2$R', —SO$_2$NR'R", and —NR'SO$_2$R", where R' and R" are individually hydrogen, lower alkyl, cycloalkyl, heterocyclyl, or an aromatic group-containing species selected from the group consisting of phenyl, benzyl, pyridinyl, pyrimidinyl, pyrazinyl, pyridazinyl, indolyl and quinolinyl, and r is an integer from 1 to 6, or R' and R" can together form a cycloalkyl group;

X' is COR' where R' is selected from the group consisting of aryl, substituted aryl, heteroaryl, substituted heteroaryl, non-aromatic heterocyclyl, substituted non-aromatic heterocyclyl, non-aromatic heterocyclylalkyl and substituted non-aromatic heterocyclylalkyl;

m is an integer and n is an integer such that the sum of m plus n is 0, 1, 2 or 3; E, E$^I$, E$^{II}$ and E$^{III}$ individually represent hydrogen or a suitable non-hydrogen substituent selected from the group consisting of alkyl, substituted alkyl, halo-substituted alkyl, cycloalkyl, substituted cycloalkyl, heterocyclyl, substituted heterocyclyl, aryl, substituted aryl, alkylaryl, substituted alkylaryl, arylalkyl and substituted arylalkyl; and Q is selected from:

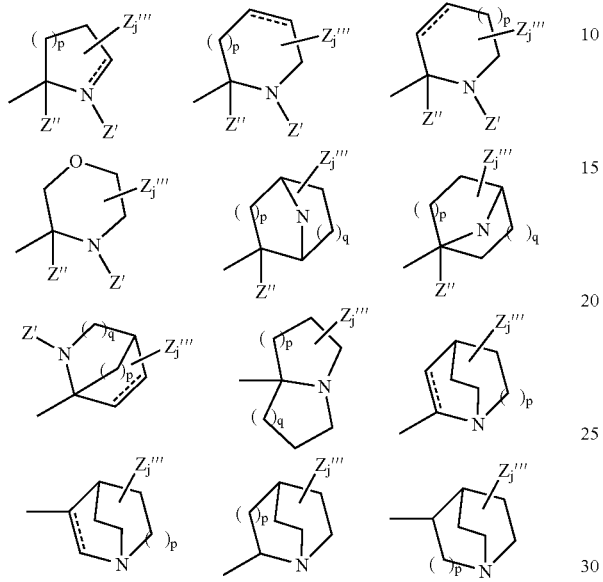

where Z' represents hydrogen or lower alkyl, acyl, alkoxycarbonyl, or aryloxycarbonyl; Z" is hydrogen or lower alkyl; arid Z''' is a non-hydrogen substituent selected from the group consisting of alkyl, substituted alkyl, halo-substituted alkyl, cycloalkyl, substituted cycloalkyl, heterocyclyl, substituted heterocyclyl, aryl, substituted aryl, alkylaryl, substituted alkylaryl, arylalkyl and substituted arylalkyl; the dotted line indicates a carbon-carbon single bond or a carbon-carbon double bond; p is 0, 1 or 2; q is 0, 1, 2 or 3; and j is an integer from 0 to 3, and a pharmaceutically acceptable carrier, wherein $Z'''_j$ refers to j number of Z''' substituents.

4. The pharmaceutical composition of claim 3, wherein Q is

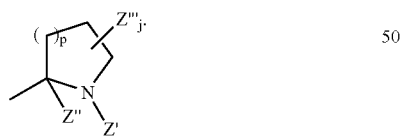

5. A method for treating a central nervous system disorder associated with dysfunction of nicotinic receptors, said method comprising of the administration of an effective amount of a compound having the formula:

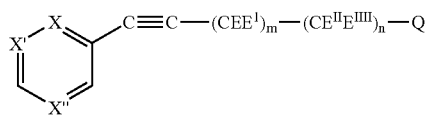

where X" is nitrogen, X and X' are individually carbon bonded to a substituent species selected from the group consisting of hydrogen, alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl; arylalkyl, substituted arylalkyl, halo, —OR', —NR'R", —CF$_3$, —CN, —NO$_2$, —C$_2$R', —SR', —N$_3$, C(=O)NR'R", —NR'C(=O)R", —C(=O)R', —C(=O)OR', —OC(=O)R', —O(CR'R")$_r$C(=O)R', —O(CR'R")$_r$NR'R" —O(CR'R")$_r$NR"C(=O)R', —O(CR'R")$_r$NR"SO$_2$R', —OC(=O)NR'R", —NR'C(=O)O R", —SO$_2$R', —SO$_2$NR'R", and —NR'SO$_2$R", where R' and R" are individually hydrogen, lower alkyl, cycloalkyl, heterocyclyl, or an aromatic group-containing species selected from the group consisting of phenyl, benzyl, pyridinyl, pyrimidinyl, pyrazinyl, pyridazinyl, indolyl and quinolinyl, and r is an integer from 1 to 6, or R' and R" can together form a cycloalkyl group;

m is an integer and n is an integer such that the sum of m plus n is 0, 1, 2 or 3; E, $E^I$, $E^{II}$ and $E^{III}$ individually represent hydrogen or a suitable non-hydrogen substituent selected from the group consisting of alkyl, substituted alkyl, halo-substituted alkyl, cycloalkyl, substituted cycloalkyl, heterocyclyl, substituted heterocyclyl, aryl, substituted aryl, alkylaryl, substituted alkylaryl, arylalkyl and substituted arylalkyl; and Q is selected from:

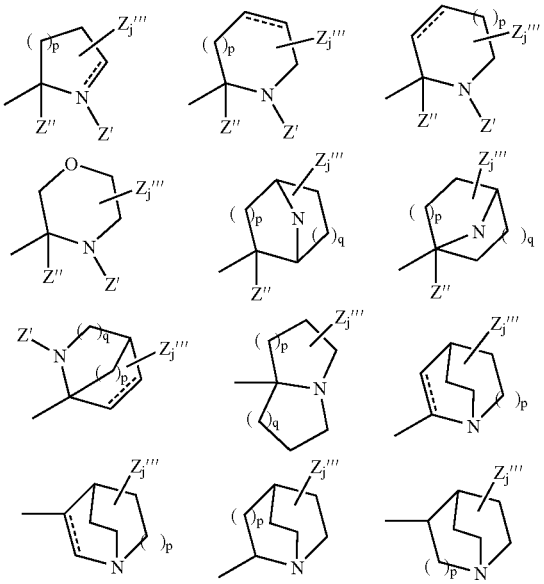

where Z' is hydrogen, lower alkyl, acyl, alkoxycarbonyl, or aryloxycarbonyl; Z" is hydrogen or lower alkyl; and Z''' is a non-hydrogen substituent selected from the group consisting of alkyl, substituted alkyl, halo-substituted alkyl, cycloalkyl, substituted cycloalkyl, heterocyclyl, substituted heterocyclyl, aryl, substituted aryl, alkylaryl, substituted alkylaryl, arylalkyl and substituted arylalkyl; the doted line indicates a carbon-carbon single bond or a carbon-carbon double bond; p is 0, 1 or 2; q is 0, 1, 2 or 3; and j is an integer from 0 to 3, wherein Z'''j refers to j number of Z''' substituents, and
wherein the central nervous system disorder is selected from the group consisting of pre-senile dementia, senile dementia, HIV-dementia, multiple cerebral infarcts, Parkinsonism, Pick's disease, Huntington's chorea, tardive dyskindesia, hyperkinesias, mania, attention deficit disorder, anxiety, depression, mild cognitive impairment, dyslexia, schizophrenia and Tourette's syndrome.

6. The method of claim 5 wherein X' is COR' where R' is selected from the group consisting of aryl, substituted aryl, heteroaryl, substituted heteroaryl, non-aromatic heterocyclyl, substituted non-aromatic heterocyclyl, non-aromatic heterocyclylalkyl and substituted non-aromatic heterocyclylalkyl.

7. The method of claim 5 wherein Q is

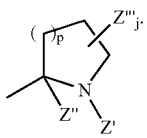

8. The method of claim 5 wherein, the compound is selected from the group consisting of (S)-5-(2-pyrrolidin-2-ylethynyl)pyridine, (R)-5-(2-pyrrolidin-2-ylethynyl)pyridine, (S)-3-isopropoxy-5-(2-pyrrolidin-2-ylethynyl)pyridine, (S)-3-phenyl-5-(pyrrolidin-2-ylethynyl)pyridine, (S)-3-(phenoxyphenyl)-5-(2-pyrrolidin-2-ylethynyl)pyridine, (S)-3-(4-methoxyphenoxy)-5-(2-pyrrolidin-2-ylethynyl)pyridine, (S)-3-(4-hydroxyphenoxy)-5-(2-pyrrolidin-2-ylethynyl)pyridine, (S)-3-cyclopentyloxy-5-(2-pyrrolidin-2-ylethynyl)pyridine, (S)-3-cyclohexyloxy-5-(2-pyrrolidin-2-ylethynyl)pyridine, (S)-3-(4-pyrrolidine-1-sulfonyl)phenoxy)-5-(2-pyrrolidin-2-ylethynyl)pyridine, (S)-3-(3-pyridyloxy)-5-(2-pyrrolidin-2-ylethynyl)pyridine, (S)-3-(pyrrolidin-2-ylethynyl)-5-(tetrahydropyran-4-yloxy)pyridine, and (S)-3-(3,5-dihydroxy)phenoxy)-5-(2-pyrrolidin-2-ylethynyl)pyridine.

* * * * *

UNITED STATES PATENT AND TRADEMARK OFFICE
CERTIFICATE OF CORRECTION

PATENT NO. : 7,101,896 B2
APPLICATION NO. : 11/039641
DATED : September 5, 2006
INVENTOR(S) : Dull et al.

It is certified that error appears in the above-identified patent and that said Letters Patent is hereby corrected as shown below:

In the Specification:

In the right-hand formula depicted at Column 6, Lines 1-5:

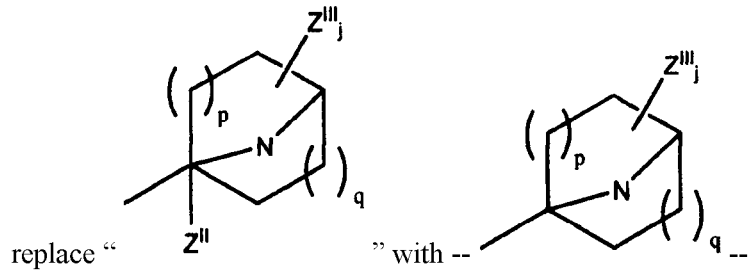

In the Claims:

The formula in Claim 1, Column 45, Line 10:

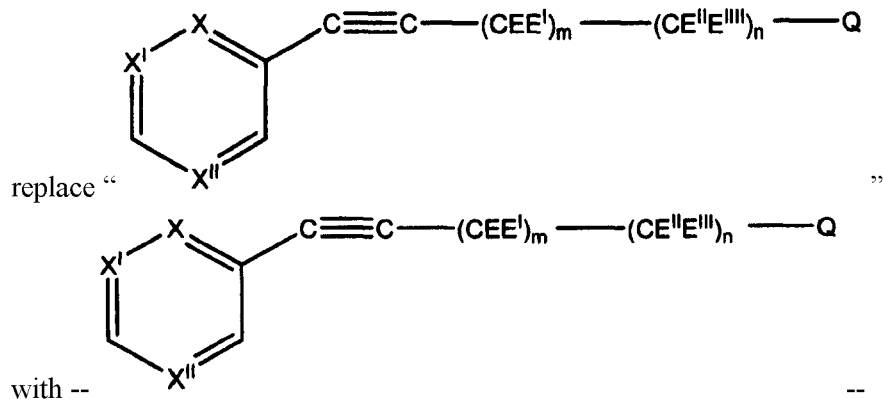

Signed and Sealed this

Thirty-first Day of August, 2010

David J. Kappos
*Director of the United States Patent and Trademark Office*

CERTIFICATE OF CORRECTION (continued)
U.S. Pat. No. 7,101,896 B2

In Claim 1, Column 45, Lines 55-60, (in the sixth structure shown in the set):

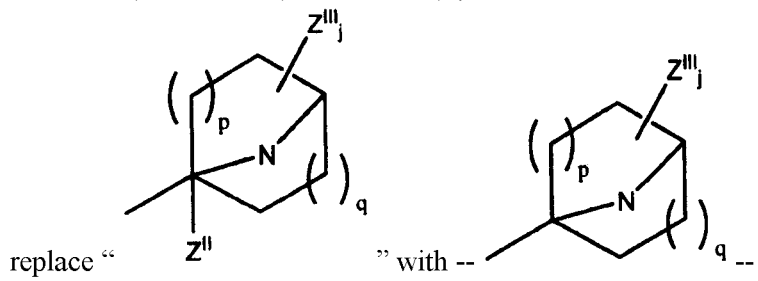

replace " [left structure] " with -- [right structure] --

The formula in Claim 3, Column 46, Line 35:

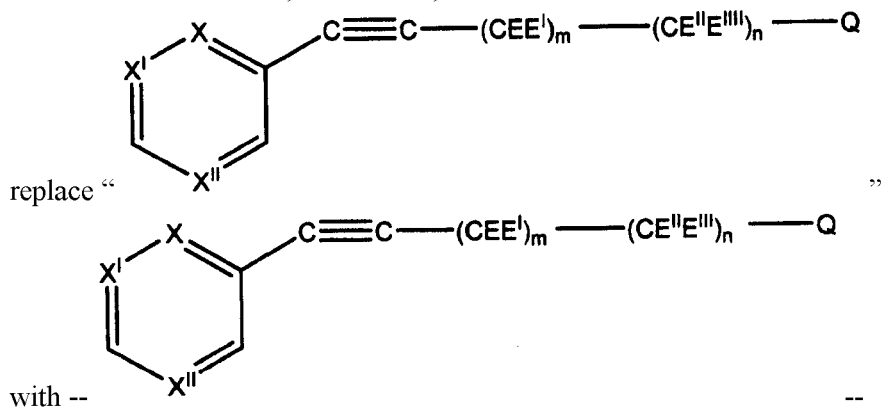

replace " [top structure] " with -- [bottom structure] --

The formula in Claim 3, Column 47, Lines 15-20 in the sixth structure shown:

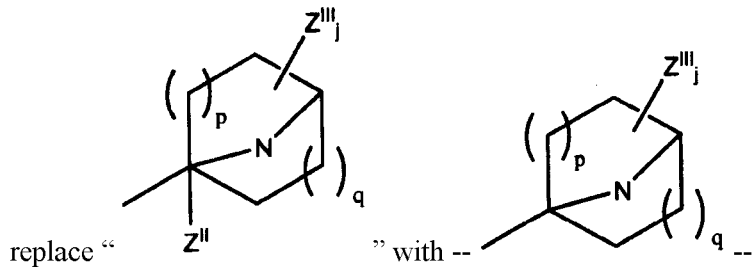

replace " [left structure] " with -- [right structure] --

In Claim 3, Column 47, Line 35, replace "arid" with -- and --

The formula in Claim 5, Column 47, Line 64:

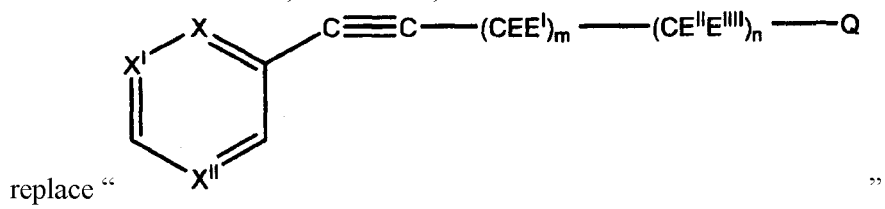

replace " [structure] "

CERTIFICATE OF CORRECTION (continued)
U.S. Pat. No. 7,101,896 B2 with -- 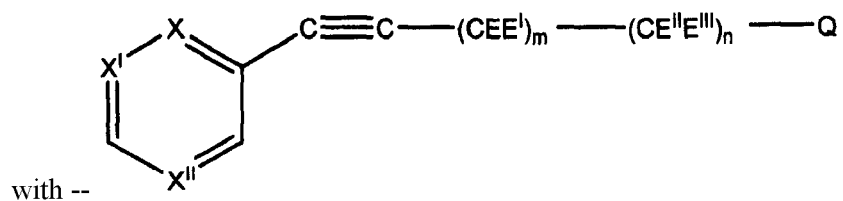 --

The formula in Claim 5, Column 48, Line 44, in the sixth structure shown:

replace " 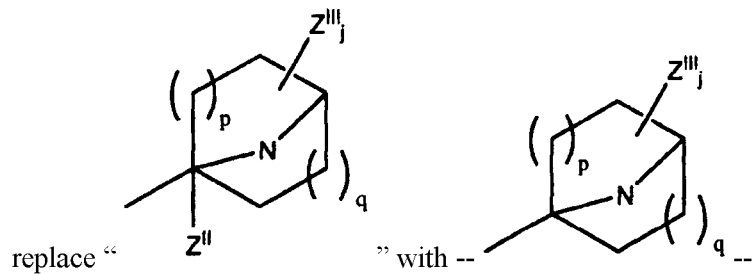 " with -- --